(12) United States Patent
Dixon et al.

(10) Patent No.: US 9,271,929 B2
(45) Date of Patent: Mar. 1, 2016

(54) BLOCK COPOLYMERS AND USES THEREOF

(75) Inventors: James Brandon Dixon, Marietta, GA (US); Jeffrey A. Hubbell, Preverenges (CH); Conlin P. O'Neil, Chavannes-renens (CH); Melody Swartz, Preverenges (CH); Diana Velluto, Lausanne (CH)

(73) Assignee: École Polytechnique Fédérale de Lausanne (EPFL), Lausanne (CH)

( * ) Notice: Subject to any disclaimer, the term of this patent is extended or adjusted under 35 U.S.C. 154(b) by 0 days.

(21) Appl. No.: 13/130,892

(22) PCT Filed: Nov. 24, 2009

(86) PCT No.: PCT/US2009/065693
§ 371 (c)(1),
(2), (4) Date: May 24, 2011

(87) PCT Pub. No.: WO2010/068432
PCT Pub. Date: Jun. 17, 2010

(65) Prior Publication Data
US 2011/0223217 A1 Sep. 15, 2011

Related U.S. Application Data

(60) Provisional application No. 61/117,892, filed on Nov. 25, 2008.

(51) Int. Cl.
*A61K 9/10* (2006.01)
*A61K 48/00* (2006.01)
(Continued)

(52) U.S. Cl.
CPC ............ *A61K 9/1075* (2013.01); *A61K 9/1273* (2013.01); *A61K 9/5146* (2013.01);
(Continued)

(58) Field of Classification Search
None
See application file for complete search history.

(56) References Cited

U.S. PATENT DOCUMENTS 4,242,474 A 12/1980 Shinohara et al.
4,618,400 A 10/1986 Wood et al.
(Continued)

FOREIGN PATENT DOCUMENTS

EP 1 932 870 A1 6/2008
EP 1932870 A1 * 6/2008
(Continued)

OTHER PUBLICATIONS

A Napoli, N Tirelli, G Kilcher, JA Hubbell. "New Synthetic Methodologies for Amphiphilic Multiblock Copolymers of Ethylene Glycol and Propylene Sulfide." Macromolecules, vol. 34, 2001, pp. 8913-8917.*

(Continued)

*Primary Examiner* — Isaac Shomer
(74) *Attorney, Agent, or Firm* — Clark & Elbing LLP

(57) ABSTRACT

An encoding/decoding apparatus and method using a low-density parity-check code (LDPC code) is disclosed. Basic column group information, serving as a set of information regarding positions of rows with weight 1, is extracted from a reference column in each column group of a predetermined parity-check matrix. Column group information transforms the positions of rows with weight 1 into positions whose lengths are within a required parity length. A parity-check matrix is generated according to the generated column group information. Data is encoded or decoded based on the generated parity-check matrix.

11 Claims, 29 Drawing Sheets

(51) Int. Cl.

| | | |
|---|---|---|
| *A61K 9/107* | (2006.01) | |
| *A61K 9/127* | (2006.01) | |
| *A61K 9/51* | (2006.01) | |
| *C08G 65/329* | (2006.01) | |
| *C08G 65/334* | (2006.01) | |
| *C08G 75/08* | (2006.01) | |
| *C08L 71/02* | (2006.01) | |
| *C08G 83/00* | (2006.01) | |
| *C08L 81/02* | (2006.01) | |

(52) U.S. Cl.
CPC .......... *C08G65/329* (2013.01); *C08G 65/3344* (2013.01); *C08G 75/08* (2013.01); *C08G 83/008* (2013.01); *C08L 71/02* (2013.01); *A61K 48/0041* (2013.01); *C08L 81/02* (2013.01); *C08L 2203/02* (2013.01); *C08L 2205/05* (2013.01); *Y10S 977/773* (2013.01); *Y10S 977/906* (2013.01); *Y10S 977/916* (2013.01)

(56) References Cited

U.S. PATENT DOCUMENTS

| | | | | |
|---|---|---|---|---|
| 4,732,938 | A | | 3/1988 | Grant et al. |
| 4,923,924 | A | | 5/1990 | Grant et al. |
| 5,268,305 | A | | 12/1993 | Ribi et al. |
| 5,294,690 | A | | 3/1994 | Iguchi et al. |
| 5,330,911 | A | | 7/1994 | Hubbell et al. |
| 5,374,668 | A | | 12/1994 | Kanemura et al. |
| 5,410,016 | A | * | 4/1995 | Hubbell et al. ............... 528/354 |
| 5,427,915 | A | | 6/1995 | Ribi et al. |
| 5,446,090 | A | | 8/1995 | Harris |
| 5,502,102 | A | | 3/1996 | Nazareth |
| 5,529,914 | A | | 6/1996 | Hubbell et al. |
| 5,567,422 | A | | 10/1996 | Greenwald |
| 5,573,934 | A | | 11/1996 | Hubbell et al. |
| 5,575,815 | A | | 11/1996 | Slepian et al. |
| 5,612,390 | A | | 3/1997 | Iguchi et al. |
| 5,635,207 | A | | 6/1997 | Grinstaff et al. |
| 5,648,506 | A | | 7/1997 | Desai et al. |
| 5,702,717 | A | | 12/1997 | Cha et al. |
| 5,752,974 | A | | 5/1998 | Rhee et al. |
| 5,801,033 | A | | 9/1998 | Hubbell et al. |
| 5,817,840 | A | | 10/1998 | Nicolaou et al. |
| 5,852,182 | A | | 12/1998 | Cook et al. |
| 5,858,746 | A | | 1/1999 | Hubbell et al. |
| 5,874,500 | A | | 2/1999 | Rhee et al. |
| 5,880,131 | A | | 3/1999 | Greenwald et al. |
| 5,897,955 | A | | 4/1999 | Drumheller |
| 5,932,462 | A | | 8/1999 | Harris et al. |
| 5,945,457 | A | | 8/1999 | Plate et al. |
| 5,965,588 | A | | 10/1999 | Vazquez et al. |
| 6,180,141 | B1 | | 1/2001 | Lemercier et al. |
| 6,224,903 | B1 | | 5/2001 | Martin et al. |
| 6,624,245 | B2 | | 9/2003 | Wallace et al. |
| 7,132,475 | B2 | | 11/2006 | Hubbell et al. |
| 2002/0041898 | A1 | * | 4/2002 | Unger et al. ............... 424/486 |
| 2003/0044468 | A1 | | 3/2003 | Cellesi et al. |
| 2003/0086964 | A1 | * | 5/2003 | Kwon et al. ............... 424/450 |
| 2003/0133963 | A1 | | 7/2003 | Hubbell et al. |
| 2003/0153001 | A1 | | 8/2003 | Soane et al. |
| 2003/0215588 | A1 | | 11/2003 | Yeager et al. |
| 2004/0234494 | A1 | * | 11/2004 | Seo et al. ............... 424/78.22 |
| 2004/0258677 | A1 | * | 12/2004 | Waldmann et al. ......... 424/130.1 |
| 2006/0057215 | A1 | | 3/2006 | Raiche et al. |
| 2006/0057222 | A1 | | 3/2006 | Linhardt et al. |
| 2006/0224095 | A1 | | 10/2006 | Claverie et al. |
| 2006/0251710 | A1 | * | 11/2006 | Kwon et al. ............... 424/450 |
| 2008/0081074 | A1 | * | 4/2008 | Gu et al. ............... 424/489 |
| 2010/0222407 | A1 | | 9/2010 | Segura et al. |

FOREIGN PATENT DOCUMENTS

| | | |
|---|---|---|
| FR | 2809617 | 12/2001 |
| GB | 1203577 | 8/1970 |
| GB | 1348045 | 3/1974 |
| JP | S62-138553 | 6/1987 |
| JP | 2000-507934 | 6/2000 |
| JP | 2001-504093 | 3/2001 |
| JP | 2003-500504 | 1/2003 |
| JP | 2004-517979 | 6/2004 |
| JP | 2005-522552 | 7/2005 |
| JP | 2005-298542 A | 10/2005 |
| JP | 2006-506335 | 2/2006 |
| JP | 2007-522274 | 8/2007 |
| WO | WO 95/13312 | 5/1995 |
| WO | WO 97/15287 | 5/1997 |
| WO | WO 97/22371 | 6/1997 |
| WO | WO-98/05269 A1 | 2/1998 |
| WO | WO 98/16202 | 4/1998 |
| WO | WO 98/32466 | 7/1998 |
| WO | WO 99/14259 | 3/1999 |
| WO | WO 99/22770 | 5/1999 |
| WO | WO 99/34833 | 7/1999 |
| WO | WO 00/09087 | 2/2000 |
| WO | WO 00/44808 | 8/2000 |
| WO | WO 00/71606 | 11/2000 |
| WO | WO 01/02017 | 1/2001 |
| WO | WO-01/32146 A2 | 5/2001 |
| WO | WO 01/92584 | 12/2001 |
| WO | WO 01/93820 | 12/2001 |
| WO | WO 02/055185 | 7/2002 |
| WO | WO 03/087223 | 10/2003 |
| WO | WO 2004/009664 | 1/2004 |
| WO | WO 2005/068533 | 7/2005 |
| WO | WO 2006/107311 | 10/2006 |
| WO | WO-2006/109945 A1 | 10/2006 |
| WO | WO 2006/137855 | 12/2006 |
| WO | WO 2006/137856 | 12/2006 |
| WO | WO-2007/008300 A2 | 1/2007 |
| WO | WO 2007008300 A2 * | 1/2007 |
| WO | WO-2007/043486 A1 | 4/2007 |
| WO | WO 2007098254 A2 * | 8/2007 |

OTHER PUBLICATIONS

S Cerritelli, A Fontana, D Velluto, M Adrian, J Dubochet, P De Maria, JA Hubbell. "Thermodynamic and Kinetic Effects in the Aggregation Behavior of a Poly(ethylene glycol-b-propylene sulfide-b-ethylene glycol) ABA Triblock Copolymer." Macromolecules, vol. 38, 2005, pp. 7845-7851.*

Y Kakizawa, K Kataoka. "Block copolymer micelles for delivery of gene and related compounds." Advanced Drug Delivery Reviews, vol. 54, 2002, pp. 203-222.*

RG Strickley. "Solubilizing Excipients in Oral and Injectable Formulations." Pharmaceutical Research, vol. 21 No. 2, Feb. 2004, pp. 201-230.*

G Thumshirn, U Hersel, SL Goodman, H Kessler. "Multimeric Cyclic RGD Peptides as Potential Tools for Tumor Targeting: Solid-Phase Peptide Synthesis and Chemoselective Oxime Ligation." Chemistry: A European Journal, vol. 9, 2003, pp. 2717-2725.*

KC Cho, SH Choi, TG Park. "Low Molecular Weight PEI Conjugated Pluronic Copolymer: Useful Additive for Enhancing Gene Transfection Efficiency." Macromolecular Research, vol. 14 No. 3, 2006, pp. 348-353.*

H Lv, S Zhang, B Wang, S Cui, J Yan. "Toxicity of cationic lipids and cationic polymers in gene delivery." Journal of Controlled Release, vol. 114, 2006, pp. 100-109.*

Aida et al., "Zinc N-substituted Porphyrins as Novel Initiators for the Living and Immortal Polymerizations of Episulfide," *Macromolecules* 23: 3887-3892, 1990.

Baker, *Controlled Release of Biologically Active Agents*, Bruck, ed., pp. 84-131 John Wiley and Sons, New York, 1987.

Ballini et al., "Amberlyst A-27, an Efficient Heterogeneous Catalyst for the Michael Reactions of Nitroalkanes with β-substituted Alkene Acceptors," *J. Org. Chem.* 61: 3209-3211, 1996.

(56) References Cited

OTHER PUBLICATIONS

Bell et al., "Transfection Mediated by Gemini Surfactants: Engineered Escape from the Endosomal Compartment," *J. Am. Chem. Soc.* 125: 1551-1558, 2003.
Bertrand et al., "Comparison of Antisense Oligonucleotides and siRNAs in Cell Culture and In Vivo," *Biochem. Biophys. Res. Commun.* 296: 1000-1004, 2002.
Blessing et al., "Different Strategies for Formation of PEGylated EGF-Conjugated PEI/DNA Complexes for Targeted Gene Delivery," *Bioconjug. Chem.* 12: 529-537, 2001.
Blume et al., "Specific Targeting with Poly(ethylene glycol)-modified Liposomes: Coupling of Homing Devices to the Ends of the Polymeric Chains Combines Effective Target Binding with Long Circulation Times," *Biochim. Biophys. Acta* 1149: 180-184, 1993.
Booth et al., "Effects of Block Architecture and Composition on the Association Properties of Poly(oxyalkylene) Copolymers in Aqueous Solution," *Macromol. Chem. Rapid Commun.* 21: 501-527, 2000.
Boyland et al., "Enzymes Catalysing Conjugations of Glutathione with Alpha-beta-unsaturated Carbonyl Compounds," *Biochem. J.* 109: 651-661, 1968.
Carlisle, "Use of Adenovirus Proteins to Enhance the Transfection Activity of Synthetic Gene Delivery Systems," *Curr. Opin. Mol. Ther.* 4: 306-312, 2002.
Chandaroy et al., "Utilizing Temperature-sensitive Association of Pluronic F-127 with Lipid Bilayers to Control Liposome-cell Adhesion," *Biochim. Biophys. Acta* 1559: 32-42, 2002.
Chasseaud, "Distribution of Enzymes that Catalyse Reactions of Glutathione with Alpha Beta-unsaturated Compounds," *Biochem. J.* 131: 765-769, 1973.
Czauderna et al., "Structural Variations and Stabilising Modifications of Synthetic siRNAs in Mammalian Cells," *Nucleic Acids Res.* 31: 2705-2716, 2003.
Deutsch et al., "Synthesis of Congeners and Prodrugs. 3. Water-soluble Prodrugs of Taxol with Potent Antitumor Activity," *J. Med. Chem.* 32: 788-792, 1989.
Discher et al., "Polymersomes: Tough Vesicles Made from Diblock Copolymers," *Science* 284: 1143-1146, 1999.
Dumitriu et al., "Polymeric Drug Carriers," in *Polymeric Biomaterials*, Dumitriu, ed., pp. 435-449 and 466-724, Marcel Dekker, New York, 1994.
Duncan et al., "Soluble Synthetic Polymers as Potential Drug Carriers," *Adv. in Polym. Sci.* 57: 51-101, 1984.
East et al., "The Mannose Receptor Family," *Biochim. Biophys. Acta* 1572: 364-386, 2002.
Eisele et al., "Kinetics of Photocrosslinking Reactions of a DCPA/EA Matrix in the Presence of Thiols and Acrylates," *J. Polym. Sci.* 35: 2333-2345, 1997.
Elbashir et al., "Duplexes of 21-Nucleotide RNAs Mediate RNA Interference in Cultured Mammalian Cells," *Nature* 411: 494-498, 2001.
Erbacher et al., "Gene Transfer by DNA/Glycosylated Polylysine Complexes into Human Blood Monocyte-Derived Macrophages," *Hum. Gene Ther.* 7: 721-729, 1996.
Fan et al., "Molecular Recognition and Catalysis: Incorporation of an "Oxyanion Hole" into a Synthetic Receptor," *New J. Chem.* 21: 81-85, 1997.
Frankel et al., "Cellular Uptake of the Tat Protein from Human Immunodeficiency Virus," *Cell* 155: 1189-1193, 1988.
Friedman et al., "Relative Nucleophilic Reactivities of Amino Groups and Mercaptide Ions in Addition Reactions with $\alpha,\beta$-Unsaturated Compounds," *J. Am. Chem. Soc.* 87: 3672-3682, 1965.
Gabizon et al., "Targeting Folate Receptor with Folate Linked to Extremities of Poly(ethylene glycol)-grafted Liposomes: In Vitro Studies," *Bioconjugate Chem.* 10: 289-298, 1999.
Ghandehari et al., "In Vitro Degradation of pH-sensitive Hydrogels Containing Aromatic Azo Bonds," *Biomaterials* 18: 861-872, 1997.
Gottschalk et al., "Folate Receptor Mediated DNA Delivery into Tumor Cells: Potosomal Disruption Results in Enhanced Gene Expression," *Gene Ther.* 1: 185-191, 1994.

Green et al., "Autonomous Functional Domains of Chemically Synthesized Human Immunodeficiency Virus Tat Trans-activator Protein," *Cell* 55: 1179-1188, 1988.
Greenwald et al., "Drug Delivery Systems: Water Soluble Taxol-2'-Poly(ethylene glycol) Ester Prodrugs-design and In Vivo Effectiveness," *J. Med. Chem.* 39: 424-431, 1996.
Greenwald et al., "Camptothecin-20-PEG Ester Transport Forms: the Effect of Spacer Groups on Antitumor Activity," *Bioorg. Med. Chem.* 6: 551-562, 1998.
Grünweller et al., "Comparison of Different Antisense Strategies in Mammalian Cells Using Locked Nucleic Acids, 2'-O-Methyl RNA, Phosphorothioates and Small Interfering RNA," *Nucleic Acids Res.* 31: 3185-3193, 2003.
Harbottle et al., "An RGD-oligolysine Peptide: a Prototype Construct for Integrin-mediated Gene Delivery," *Hum. Gene Ther.* 9: 1037-1047, 1998.
Hern et al., "Incorporation of Adhesion Peptides into Non-adhesive Hydrogels Useful for Tissue Resurfacing," *J. Biomed. Mater. Res.* 39: 266-276, 1998.
Hirai et al., "Ph-induced Structure Change of Poly(vinyl alcohol) Hydrogel Crosslinked with Poly(acrylic acid)," *Die Angewandte Makromolekulare Chemie* 240: 213-219, 1996.
Inoue et al., "Gene Therapy of Human Bladder Cancer with Adenovirus-mediated Antisense Basic Fibroblast Growth Factor," *Clinical Cancer Research* 6: 4422-4431, 2000.
Ishihara et al., "Tris(pentafluorphenyl)boron as an Efficient, Air Stable, and Water Tolerant Lewis Acid Catalyst," *Bull. Chem. Soc. Jpn.* 68: 1721-1730, 1995.
Jousma et al., "Characterization of Liposomes. The Influence of Extrusion of Multilamellar Vesicles Through Polycarbonate Membranes on Particle Size, Particle Size Distribution and Number of Bilayers," *Int. J. Pharm.* 35: 263-274, 1987.
Kabanov et al., "Pluronic® Block Copolymers as Novel Polymer Therapeutics for Drug and Gene Delivery," *J. Control Release* 82: 189-212, 2002.
Katayose et al., "Water-soluble Polyion Complex Associates of DNA and Poly(ethylene glycol)-poly(L-lysine) Block Copolymer," *Bioconjug. Chem.* 8: 702-707, 1997.
Kawai et al., "New Application of Solid Acid to Carbon-Carbon Bond Formation Reactions: Clay Montmorillonite-catalyzed Aldol Reactions of Silyl Enol Ethers with Aldehydes and Acetals," *Bull. Chem. Soc. Jpn.* 61: 1237-1245, 1988.
Kircheis et al., "Coupling of Cell-Binding Ligands to Polyethylenimine for Targeted Gene Delivery," *Gene Ther.* 4: 409-418, 1997.
Kito et al., "Biocompatible Coatings for Luminal and Outer Surfaces of Small-caliber Artificial Grafts," *Journal of Biomedical Materials Research* 30: 321-330, 1996.
Kopecek et al., "Controlled Release of Drug Model from N-(2-hydroxypropyl)-methacrylamide Copolymers," *Ann. N.Y. Acad. Sci.* 446: 93-104, 1985.
Lasic et al., *Stealth Liposomes*, Chapters 2, 4, and 9, CRC Press: Boca Raton, FL, 1995.
Lau et al., "Conjugation of Doxorubicin to Monoclonal Anti-Carcinoembryonic Antigen Antibody via Novel Thiol-directed Cross-linking Reagents," *Bioorg. Med. Chem.* 3: 1299-1304, 1995.
Lau et al., "Novel Doxorubicin-monoclonal Anti-carcinoembryonic Antigen Antibody Immunoconjugate Activity In Vitro," *Bioorg. Med. Chem.* 3: 1305-1312, 1995.
Mathur et al., "Methods for Synthesis of Hydrogel Networks: A Review," *J.M.S-Rev. Macromol. Chem. Phys.* C36: 405-430, 1996.
McCaffrey et al., "RNA Interference in Adult Mice," *Nature* 418: 38-39, 2002.
Moghaddam et al., "Molecular Design of Three-dimensional Artificial Extracellular-matrix Photosensitive Polymers Containing Cell Adhesive Peptide," *J. Polymer Sci.* 51: 1589-1597, 1993.
Morpurgo et al., "Preparation and Characterization of Poly(ethylene glycol) Vinyl Sulfone," *Bioconjug. Chem.* 7: 363-368, 1996.
Mortensen, "Block Copolymer in Aqueous Solution: Micelle Formation and Hard-Sphere Crystallization," *Prog. Colloid. Polym. Sci.* 93: 72-75, 1993.

(56) References Cited

OTHER PUBLICATIONS

Napoli et al., "New Synthetic Methodologies for Amphiphilic Multiblock Copolymers of Ethylene Glycol and Propylene Sulfide," *Macromolecules* 34: 8913-8917, 2001.
Napoli et al., "Lyotropic Behavior in Water of Amphiphilic ABA Triblock Copolymers Based on Poly(Propylene Sulfide) and Poly(Ethylene Glycol)," *Langmuir* 18: 8324-8329, 2002.
Napoli et al., "Oxidation-Responsive Polymeric Vesicles," *Nat. Mater.* 3: 183-189, 2004.
Pathak et al., "Rapid Photopolymerization of Immunoprotective Gels in Contact with Cells and Tissue," *J. Am. Chem. Soc.* 114: 8311-8312, 1992.
Pató et al., "Polymers Containing Enzymatically Degradable Bonds, 9a) Chymotrypsin Catalyzed Hydrolysis of a p-nitroanilide Drug Model, Bound Via Oligopeptides onto Poly(vinylpyrrolidone-co-maleic anhydride)," *Makromol. Chem.* 185: 231-237, 1984.
Pendri et al. "Antitumor Activity of Paclitaxel-2'-glycinate Conjugated to Poly(ethylene glycol): a Water-soluble Prodrug," *Anticancer Drug Des.* 13: 387-395, 1998.
Petka et al., "Reversible Hydrogels from Self-assembling Artificial Proteins," *Science* 281: 389-392, 1998.
Pitt et al., "Controlled Drug Delivery," in *Biodegradation of Polymers, Basic Concepts*, vol. 1, pp. 53-80, CRC Press, Boca Raton, FL, 1983.
Reich et al., "Small Interfering RNA (siRNA) Targeting VEGF Effectively Inhibits Ocular Neovascularization in a Mouse Model," *Mol. Vis.* 9: 210-216, published 2003.
Romanowska et al., "Michael Additions for Syntheses of Neoglycoproteins," *Methods in Enzymol.* 242: 90-101, 1994.
Sawhney et al., "Bioerodible Hydrogels Based on Photopolymerized Poly(ethylene glycol)-co-Poly(α-hydroxy acid) Diacrylate Macromers," *Macromolecules* 26: 581-587, 1993.
Simeoni et al., "Insight into the Mechanism of the Peptide-Based Gene Delivery System MPG: Implications for Delivery of siRNA into Mammalian Cells," *Nucleic Acids Res.* 31: 2717-2724, 2003.
Tanaka et al., "Michael-type Addition of Illudin S, a Toxic Substance from Lampteromyces japonicus, with Cysteine and Cysteine-Containing Peptides In Vitro, " *Chem. Pharm. Bull.* 44: 273-279, 1996.
Torchilin et al., "Poly(ethylene glycol) on the Liposome Surface: on the Mechanism of Polymer-coated Liposome Longevity," *Biochim. Biophys. Acta* 1195: 11-20, 1994.
Watanabe et al., "First Example of Photoinduced Copolymerizability Enhancement. Copolymerization of Epoxide and Episulfide Initiated with Zinc N-substituted Porphyrin under Visible Light Irradiation," *Macromolecules* 24: 3970-3972, 1991.
West et al., "Comparison of Covalently and Physically Cross-linked Polyethylene Glycol-based Hydrogels for the Prevention of Postoperative Adhesions in a Rat Model," *Biomaterials* 16: 1153-1156, 1995.
Won et al., "Giant Wormlike Rubber Micelles," *Science* 283: 960-963, 1999.
Wright et al., *The Chemistry and Pharmacology of Taxol and Its Derivatives*, Farina, ed., pp. 110-130 and 165-300, Elsevier, New York, 1995.
Yu et al., "Bilayer Morphologies of Self-assembled Crew-cut Aggregates of Amphiphilic PS-b-PEO Diblock Copolymers in Solution," *Macromolecules* 31: 3509-3518, 1998.
Zalipsky et al., "Attachment of Drugs to Polyethylene Glycols," *Eur. Polym. J.* 19: 1177-1183, 1983.
Zalipsky et al., "Peptide Attachment to Extremities of Liposomal Surface Grafted PEG Chains: Preparation of the Long-circulating Form of Laminin Pentapeptide, YIGSR," *Bioconjugate Chem.* 6: 705-708, 1995.
Zalipsky, "Long-circulating, Polyethylene Glycol-grafted Immunoliposomes," *J. Control. Release* 39: 153-161, 1996.
Zhao et al., "Novel Degradable PEG Esters for Drug Delivery: Synthesis and Characterization," *Polymer Reprints* 38: 526-527, 1997.
Zhou et al., "Self-Assembly in a Mixture of Two Poly(Ethylene Oxide)-b-Poly(Propylene Oxide)-b-Poly(Ethylene Oxide) Copolymers in Water," *J. Colloid Interface Sci.* 183: 339-350, 1996.
International Preliminary Report on Patentability for International Application No. PCT/US2009/65693, dated May 31, 2011.
International Search Report for International Application No. PCT/US09/65693, dated Jan. 20, 2010.
Dahlqvist et al., "The digestion and absorption of sucrose by the intact rat," J Physiol. 167:193-209 (1963).
Davies et al., "Self-assembly of surfactant vesicles that transform into viscoelastic wormlike micelles upon heating," J Am Chem Soc. 128(20):6669-75 (2006).
Chen et al., "pH-responsive biodegradable micelles based on acid-labile polycarbonate hydrophobe: synthesis and triggered drug release," Biomacromolecules. 10(7):1727-35 (2009).
Supplementary European Search Report issued for European Patent Application 09832335.5, mailed Apr. 14, 2015 (8 pages).
Loh et al., "The in vitro hydrolysis of poly(ester urethane)s consisting of poly[(R)-3-hydroxybutyrate] and poly(ethylene glycol)," Biomaterials. 27(9):1841-50 (2006).
Partial European Search Report issued for European Patent Application 09832335.5, mailed Dec. 9, 2014 (8 pages).
Sowter et al., "Predominant role of Hypoxia-inducible transcription factor (Hif)-1alpha versus Hif-2alpha in regulation of the transcriptional response to hypoxia," Cancer Res. 63: 6130-6134, 2003.
"pH-responsive polymeric siRNA carriers sensitize multidrug resistant ovarian cancer cells to doxorubicin via knockdown of polo-like kinase 1," available in PMC Aug. 11, 2010, published in final edited form as: Mol Pharm. 7(2): 442-455 (2010) (24 pages).
Inoue et al., "Nanometer-scale patterning of self-assembled monolayer films on native silicon oxide," Appl Phys Lett. 73(14):1976-8 (1998).
Kenausis et al., "Poly(l-lysine)-g-poly(ethylene glycol) layers on metal oxide surfaces: Attachment mechanism and effects of polymer architecture on resistance to protein adsorption," J Phys Chem B. 104(14):3298-3309 (2000).
Liebau et al., "Microcontact Printing with Heavyweight Inks," Advanced Functional Materials. 11(2):147-50 (2001).
Mühl et al., "Parallel nanolithography in carbon layers with conductive imprint stamps," Appl Phys Lett. 76(6):786-88 (2000).
NCBI Blast for Accession No. NP_001079500. Retrieved on Nov. 14, 2012 (2 pages).
Ryter et al., "Molecular basis of double-stranded RNA-protein interactions: structure of a dsRNA-binding domain complexed with dsRNA," EMBO J. 17(24): 7505-7513 (1998).

\* cited by examiner

A

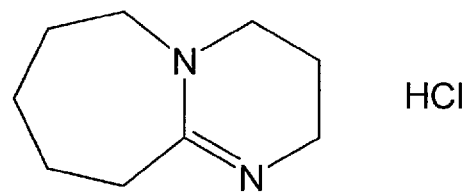
1,8-Diazabicyclo[5.4.0]undec-7-ene
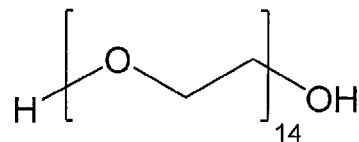
Polyethylene glycol Mw 400
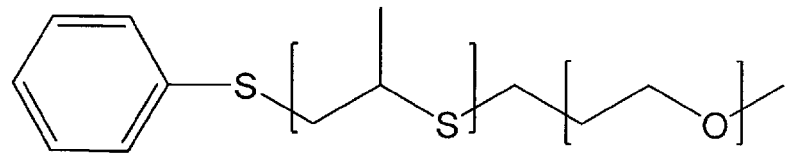
Poly(ethylene glycol)-*bl*-Poly(propylene sulfide) (PEG-PPS)
FIGURE 3

A

B

|  | Mp | Mn | Mw | PDI |
|---|---|---|---|---|
| AVG | 3677.96 | 3451.46 | 4098.65 | 1.19 |
| STDEV | 87.69 | 143.02 | 137.55 | 0.01 |
| %CV | 2.4% | 4.1% | 3.4% | 1.2% |

| | PEG | | PPS | | | Benzene | | |
| | CH3 (1) | CH2CH2O (2) | CH (3) | CH2 (4) | CH3 (5) | CH (6) | CH (7) | CH (8) |
|---|---|---|---|---|---|---|---|---|
| Control | 3.006 | 183.782 | 12.396 | 24.222 | 37.684 | 1.996 | 1.998 | 1.012 |
| Heated | 2.950 | 183.782 | 12.109 | 24.697 | 37.584 | 1.991 | 2.039 | 1.075 |
| Heat+Salt | 2.978 | 183.782 | 12.129 | 24.732 | 37.396 | 1.918 | 2.008 | 1.061 |
| Average | 2.98 | 183.78 | 12.21 | 24.55 | 37.55 | 1.97 | 2.02 | 1.05 |
| Std. Dev. | 0.03 | 0.00 | 0.16 | 0.28 | 0.15 | 0.04 | 0.02 | 0.03 |
| %CV | 0.9% | 0.0% | 1.3% | 1.2% | 0.4% | 2.2% | 1.1% | 3.2% |

| Sample | PEG-PPS | Mix | | Salt | | |
|---|---|---|---|---|---|---|
| Peak | 1 | 1 | 2 | 1 | 2 | 3 |
| Average | 48.15 | 47.65 | 104.86 | 44.92 | 89.95 | 118.40 |
| STDEV | 0.78 | 1.28 | 8.70 | 0.20 | 0.76 | 4.58 |
| %CV | 1.6% | 2.7% | 8.3% | 0.4% | 0.8% | 3.9% |

A

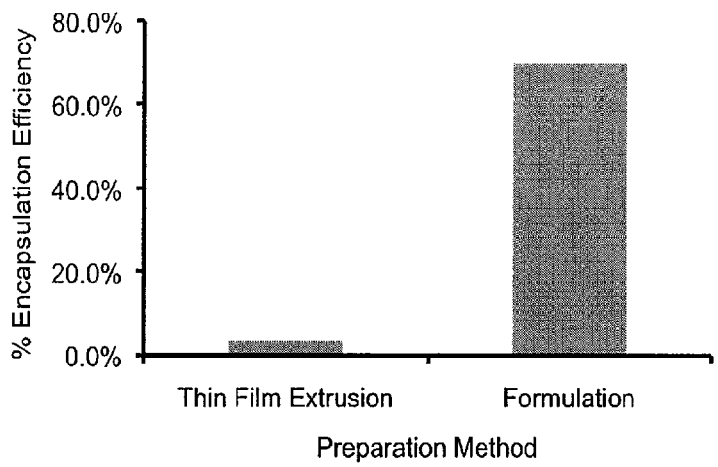

B

| Formulation | Drug | PEG-PPS | E. Efficiency | Loading |
|---|---|---|---|---|
| Control | Dexamethasone | EG46-PS21 | 88.7% | 8.3% |
| PEG600 | Dexamethasone | EG46-PS21 | 64.5% | 65.2% |
| PEG600 | Dexamethasone | EG46-PS10 | 36.1% | 4.5% |
| Control | Paclitaxel | EG46-PS21 | 30.4% | 4.6% |
| PEG600 | Paclitaxel | EG46-PS21 | 8.1% | 10.9% |
| PEG600 | Paclitaxel | EG46-PS10 | 96.2% | 14.6% |

C

Encapsulation efficiency using the direct hydration method with PEG 500 DME

| Polymer | Protein | Protein added (μg)[a] | Protein encapsulated (μg)[a] | Protein loading, mean ± SD (μg/mg) | Encapsulation efficiency, mean ± SD (%) |
|---|---|---|---|---|---|
| $EG_{46}\text{-}PS_{66}$ | bSA | 281.9 | 15.4 ± 15.1 | 1.5 ± 1.5 | 5.5 ± 5.4 |
| $EG_{46}\text{-}PS_{66}$ | bSA | 659.2 | 128.0 ± 32.6 | 12.8 ± 3.3 | 19.4 ± 4.9 |
| $EG_{46}\text{-}PS_{66}$ | bSA | 659.2 | 61.9 ± 6.9 | 6.2 ± 0.7 | 8.4 ± 10.5 [b] |
| $EG_{46}\text{-}PS_{66}$ | Ova | 43.6 | 10.4 ± 7.4 | 1.0 ± 0.7 | 23.9 ± 17.1 |
| $EG_{46}\text{-}PS_{66}$ | Ova | 83.0 | 25.2 ± 4.7 | 2.5 ± 0.5 | 30.3 ± 5.7 |
| $EG_{46}\text{-}PS_{66}$ | β-Gal | 0.01 | 0.0 ± 0.0 | 0.0 ± 0.0 | 0.0 ± 0.0 |

[a] Per 10 mg copolymer
[b] bSA freeze dried and formulated with polymer and PEG 500 DME

FIGURE 11

Dynamic Light Scattering (DLS): determines the size distribution of small particles in diluted solution
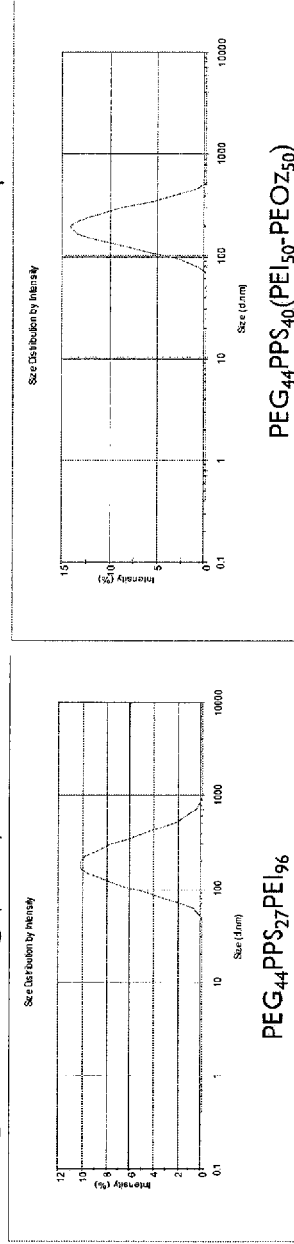
Cryo-Trasmission Electron Myscroscopy (Cryo-TEM): yields insight into aggregate morphology. Samples need to be highly concentrated (8mg/mL)
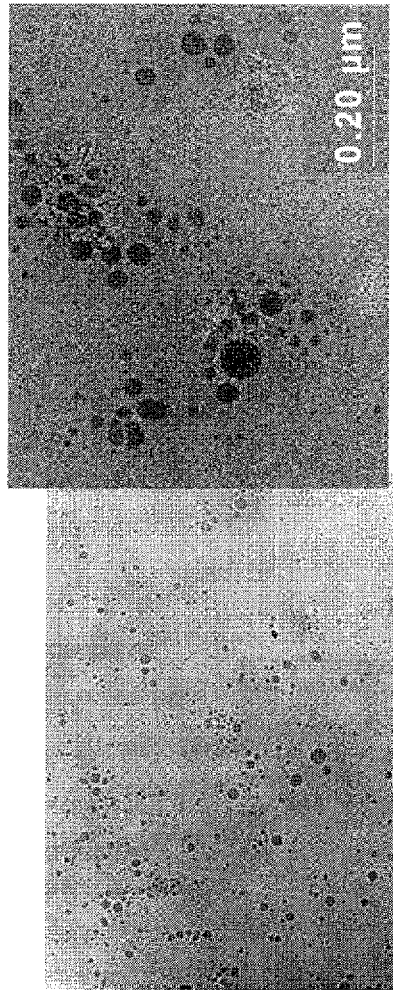
More packed aggregates: PEI chains are not completely extended
FIGURE 19

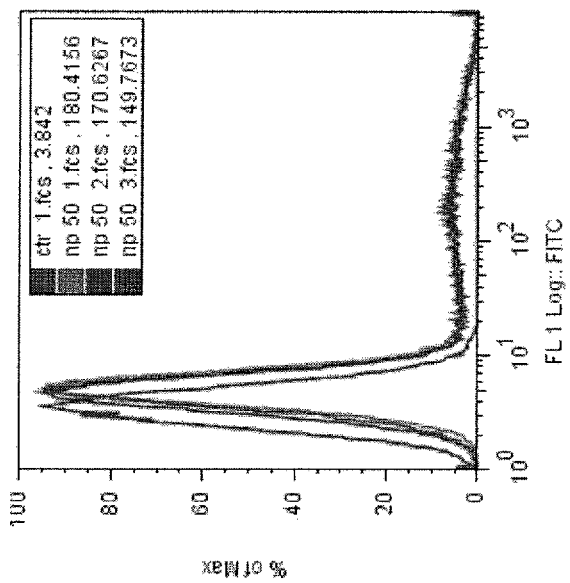
| TB-copolymer-DNA | serum | Incubation time | Time between transfection and counting |
|---|---|---|---|
| PEG2k-PPS27-PEI6 | Yes | 24h | 48h |
47% cells transfected (FACS analysis)
FIGURE 20

PEG$_{44}$ - PPS$_{27}$ - PEI$_{96}$

| Sample | Polymer | siRNA |
|---|---|---|
| 1 | 0 | 100 pmole |
| 2 | 10µg | 100 pmole |
| 3 | 20µg | 100 pmole |
| 4 | 30µg | 100 pmole |
| 5 | 50µg | 100 pmole |
| 6 | 95µg | 100 pmole |

PEG$_{44}$-PPS$_{20}$ & PPS$_{10}$-PEI$_{50}$

| Sample | Polymer | siRNA |
|---|---|---|
| 1 | 120µg | 100 pmole |
| 2 | 240µg | 100 pmole |
| 3 | 360µg | 100 pmole |
| 4 | 600µg | 100 pmole |
| 5 | 1140µg | 100 pmole |
| 6 | 0 | 100 pmole |

BLOCK COPOLYMERS AND USES THEREOF

CROSS-REFERENCE TO RELATED APPLICATIONS

This application is the national stage of International Application No. PCT/US2009/065693, filed Nov. 24, 2009, which claims benefit of U.S. Provisional Application No. 61/117,892, filed Nov. 25, 2008, which is hereby incorporated by reference.

BACKGROUND OF THE INVENTION

The invention relates to the field of polymer chemistry.

In the field of pharmaceutical agent delivery there exists an extensive interest in amphiphilic block copolymers that can self-assemble in aqueous environments into stable supramolecular structures. A variety of supramolecular structures can be generated such as micellar and vesicular assemblies, both of which can be important for pharmacological applications. Extensive investigations have been conducted in poly(ethylene glycol) (PEG)-containing block copolymers, such as copolymers with poly(propylene glycol) and poly(ethylethylene). Such block copolymers are generally prepared via ionic polymerization under strictly anhydrous conditions, making it difficult to obtain asymmetric block copolymers or to introduce biological molecules.

Accordingly, there is a need for new block copolymers.

SUMMARY OF THE INVENTION

Block copolymers containing charged blocks or chemical moieties sensitive to oxidation or hydrolysis have been developed. We describe the use of such block copolymers in supramolecular structures, e.g., micelles or vesicles, and pharmaceutical compositions and in methods of preparing the supramolecular structures and pharmaceutical compositions. The invention is particularly useful for the delivery of pharmaceutical agents, e.g., nucleic acids, to cells.

Accordingly, in one aspect, the invention features a block copolymer including a hydrophilic block and a hydrophobic block wherein at least one of the blocks is interrupted with a hydrolysable or oxidation-sensitive chemical moiety. Desirably, the block copolymer is capable of self-assembling into a supramolecular structure, such as a micelle or vesicle. In certain embodiments, the hydrolysable chemical moiety is an ester, amide, thioester, anhydride, or ketal. In another embodiment, the hydrophilic block is poly(ethylene glycol) (PEG), and the hydrophobic block is poly(propylene sulfide) (PPS).

In another aspect, the invention features a supramolecular structure, e.g., a micelle or a vesicle, containing (i) a block copolymer of a hydrophilic block and a hydrophobic block and (ii) an excipient. Desirably, the excipient is an amphipathic molecule. In preferred embodiments, the excipient is 1,8-diazabicyclo[5.4.0]undec-7-ene (DBU) or PEG of molecular weight between 400 and 800. The supramolecular structure may further contain a hydrophobic or hydrophilic pharmaceutical agent. The pharmaceutical agent is, for example, a peptide, a nucleic acid, an antibiotic, or a chemotherapeutic drug. In certain embodiments, the pharmaceutical agent is selected from dexamethasone, paclitaxel, cyclosporine A, sirolimus, everolimus, tacrolimus, amphotericin B, or adriamycin. In other embodiments, the pharmaceutical agent is a polypeptide, such as a protein or an antibody or an antigen-binding fragment of an antibody. In preferred embodiments, the pharmaceutical agent is encapsulated in the supramolecular structure at an efficiency greater than 5%, 25%, 50%, 75%, 90%, or even 95%. The supramolecular structure may be included in a pharmaceutical composition with a pharmaceutically acceptable diluent.

In a related aspect, the invention features a method of encapsulating a pharmaceutical agent in a supramolecular structure, e.g., a micelle or a vesicle. The method includes contacting the pharmaceutical agent with an excipient and a block copolymer containing a hydrophilic block and a hydrophobic block, applying heat to homogenize the mixture of the pharmaceutical agent, excipient, and block copolymer, and diluting the homogenized mixture in an aqueous solution. In certain embodiments, the excipient is DBU or PEG of molecular weight between 400 and 800.

The invention further features a method of making a vesicle including forming micelles from a block copolymer containing a hydrophilic block and a hydrophobic block, wherein a vesicle formed by the block copolymer is thermodynamically more stable than a micelle formed by the block copolymer, and heating the micelles to form the vesicle. In certain embodiments, the vesicles formed by the method are 70 to 800 nm in diameter. In other embodiments, the micelles are suspended in a solution containing a pharmaceutical agent, and the pharmaceutical agent is encapsulated in the vesicles upon heating the solution. In another embodiment, the hydrophilic block of the block copolymer contains PEG, and the hydrophobic block of the block copolymer contains PPS. The invention also provides a vesicle prepared by this method.

In another aspect, the invention features a dry formulation containing micelles of a block copolymer having a hydrophilic block and a hydrophobic block, wherein the water content of the formulation is less than 5%, e.g., less than 2%. The dry formulation may further contain a pharmaceutical agent. In certain embodiments, the hydrophilic block of the block copolymer contains PEG, and the hydrophobic block of the block copolymer contains PPS.

The invention further features a supramolecular structure containing a block copolymer containing a positively charged block and a nucleic acid, wherein the supramolecular structure has a maximal diameter of less than 60 nm. The block copolymer may further include a hydrophilic block, e.g., PEG, and a hydrophobic block, e.g., PPS. In one embodiment, the block copolymer contains PPS, PEG, and polyethylene imine (PEI). In another embodiment, the nucleic acid is a single-stranded oligonucleotide, a short interfering RNA, an aptamer, or plasmid DNA. Desirably, the maximal diameter of the supramolecular structure is less than 40 nm. In a related aspect, the invention features a method of transfecting a cell with a nucleic acid including contacting the cell with a supramolecular structure containing a block copolymer containing a positively charged block and the nucleic acid.

In another aspect, the invention features a block copolymer containing PPS, PEG, and PEI. In certain embodiments, the PPS block and the PEI block are attached via a bond that is labile in an endosome, e.g., a disulfide bond, vinyl ether, orthoester, acyl hydrazone, or a —N—PO$_3$— group. In another embodiment, the block copolymer includes a nucleic acid that is bound to the PEI block. The block copolymer may be included in a pharmaceutical composition containing a pharmaceutical agent and a pharmaceutically acceptable diluent.

The invention further features a micelle between 10 and 60 nm in diameter containing two block copolymers, the first of which contains a hydrophilic block and a hydrophobic block, the second of which contains a hydrophilic block, a hydrophobic block, and a positively charged block. In one particular embodiment, the first block copolymer contains PEG and PPS, and the second block copolymer contains PEG, PPS, and PEI. In other embodiments, the micelle has a maximal diameter between 20 and 50 nm. The micelle may be included in a pharmaceutical composition containing a pharmaceutical agent and a pharmaceutically acceptable diluent.

In another aspect, the invention features a supramolecular structure containing block copolymers containing a hydrophilic block, e.g., PEG, and a hydrophobic block, e.g., PPS, wherein 5-25% of the repeating units in the block copolymer have a charged chemical moiety disposed at the outer surface of the supramolecular structure. In certain embodiments, the charged chemical moiety is carboxylic acid, sulfate, or sulfone. The supramolecular structure may be included in a pharmaceutical composition containing a pharmaceutical agent and a pharmaceutically acceptable diluent.

In any of the embodiments of the invention, the hydrophilic block may contain poly(ethylene glycol), poly(ethylene oxide)-co-poly(propylene oxide) di- or multiblock copolymers, poly(ethylene oxide), poly(vinyl alcohol), poly(ethylene-co-vinyl alcohol), poly(N-vinyl pyrrolidone), poly(acrylic acid), poly(ethyloxazoline), poly(alkylacrylates), poly(acrylamide), poly(N-alkylacrylamides), polypeptide, polysaccharide, poly(N,N-dialkylacrylamides), hyaluronic acid, or poly(N-acryloylmorpholine). The hydrophobic block may contain poly(propylene sulfide), poly(propylene glycol), esterified poly(acrylic acid), esterified poly(glutamic acid), esterified poly(aspartic acid), or a polypeptide. In certain embodiments, the charged block is PEI, a polypeptide, poly(amidoamine), poly(sodium 1-(N-acryloylpiperazin-1-yl)diazen-1-ium-1,2-diolate), poly(sodium 1-(N-acryloylhomopiperazin-1-yl)diazen-1-ium-1,2-diolate) or poly(sodium 1-(N-acryloyl-2,5-dimethylpiperazin-1-yl)diazen-1-ium-1,2-diolate).

By a "block copolymer" is meant a compound containing at least two blocks that each contain two or more repeating units of a chemical moiety. The chemical moiety of one block is distinct from a chemical moiety present in another block of the block copolymer. For example, a block copolymer may contain a poly(ethyleneglycol) (PEG) block and a poly(propylene sulfide) (PPS) block. Typically, the number of repeating units in a block is between 4 and 250. An exemplary hydrophilic block contains up to 250 repeating units, and an exemplary hydrophobic block contains up to 100 repeating units. Repeating units of a block may be interrupted or modified by a group that confers a desirable functionality, e.g., the ability to be hydrolyzed.

By a block that is "interrupted with" a hydrolysable chemical moiety is meant a block of the same repeating unit that includes within it the hydrolysable chemical moiety so that, when the chemical moiety is hydrolyzed, the number of repeating units in the block decreases. Upon hydrolysis, the block may decrease in size by at least, e.g., 2, 4, 10, 15, 20, 30, 50, 75, 100, or 115 repeating units. Hydrolysable moieties include, e.g., esters, amides, thioesters, anhydrides, and ketals. An exemplary block that is interrupted with a hydrolysable chemical moiety is $PEG_{46}$ esterified to $PEG_4$.

By a "hydrolysable chemical moiety" is meant a chemical moiety that is cleaved in aqueous solution with a half life of 1 year or less at pH 7.4 and 37° C. Preferably, the half life of the moiety at pH 7.4 and 37° C. is one month or less.

By "nucleic acid" is meant any nucleobase oligomer. For the purposes of this specification, modified oligonucleotides that do not have a phosphorus atom in their internucleoside backbone are also considered to be nucleobase oligomers. Non-limiting examples of nucleic acids are antisense oligonucleotides, small interfering RNAs (siRNAs), aptamers, and plasmid DNA.

BRIEF DESCRIPTION OF THE DRAWINGS

FIG. 3. Formulation excipients DBU and PEG600 were blended with the block copolymer PEG-PPS at 95° C. with stirring.

FIG. 11A. Encapsulation efficiency of DBU-HCl formulation compared to thin film hydration with extrusion. Ovalbumin was reduced using TCEP and purified using Sephadex G50 and freeze-dried. 26 mg of the reduced ovalbumin was dissolved in 500 µl of distilled water and added to a preparation of PEG-PPS blended with DBU-HCl at 95° C. for 15 min. Above, 10 µl of this solution was added, mixed, and slowly diluted with distilled water. Results were calculated from a standard curve made with the same reduced ovalbumin sample. Thin film hydration with extrusion results were taken from Jousma et al Int. J. Pharm. 35 (1987) 263-274.

FIG. 11B. Encapsulation efficiency of dexamethasone and paclitaxel in PEG formulations. Dexamethasone or paclitaxel were incubated with the indicated block copolymers and the indicated PEG or control formulations according to the methods of the invention.

FIG. 11C. Bovine serum albumin and ovalbumin were prepared at 50 mg/mL in distilled water. The formulations were prepared as follows. Ten milligrams of PEG-PPS was heated with 10 mg of PEG500 dimethyl ether and heated at 95° C. for 15 minutes. The melt was mixed and allowed to cool to room temperature. After, a volume of protein solution (5 µL or 10 µL) was added and slowly diluted with distilled water up to 1 mL volume with mixing. To calculate the encapsulation efficiencies, standard curves were generated for both BSA (using fluorescamine) or ovalbumin (using FITC-ovalbumin). The dispersed vesicle solutions were centrifuged for 10 minutes at 10,000 g to sediment the vesicles, and we measured the free protein in the supernatant.

FIG. 19. PEG-PPS-PEI was demonstrated to condense plasmid DNA into nanoparticles of size distribution for transfection.

FIG. 20. PEG-PPS-PEI was demonstrated to transfect cells very efficiently, even difficult-to-transfect cells such as 3T3 fibroblasts, shown here. Other cells were transfected at even higher transfection efficiency, including 239T cells at 96% with PEG2 kDa-$PPS_{27}$-$PEI_{96}$.

DETAILED DESCRIPTION OF THE INVENTION

Figure 1A:
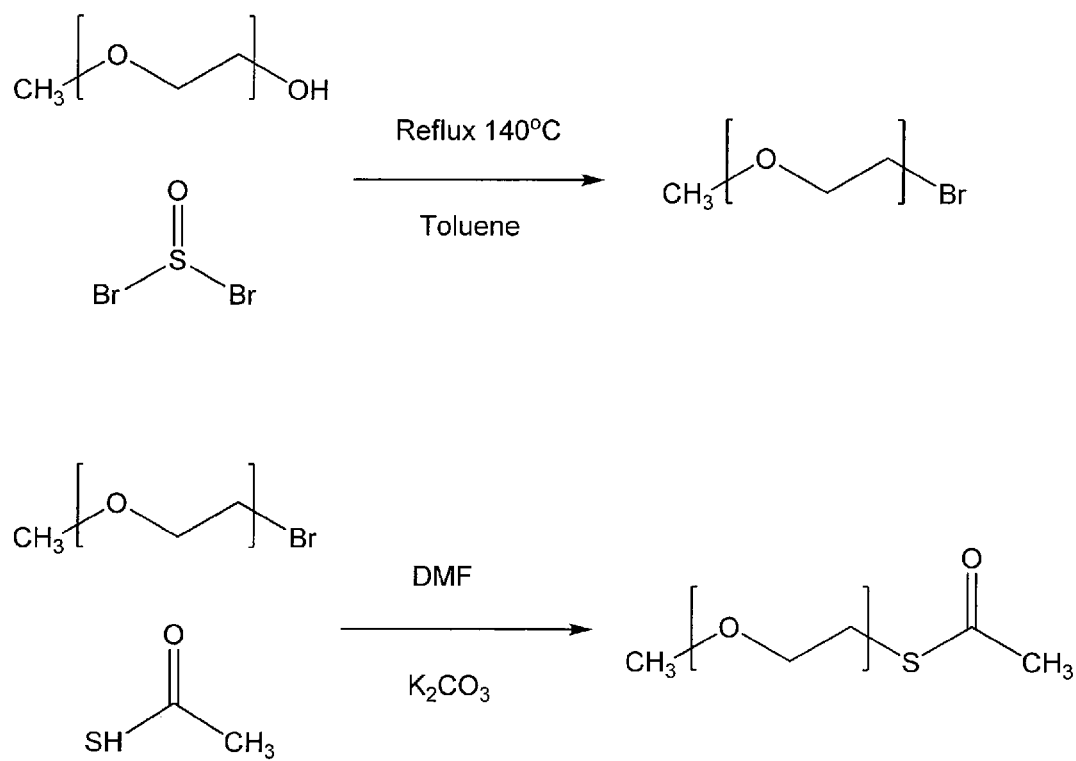
FIG. 1A. Conversion of poly(ethylene glycol)monomethyl ether (PEG MME) to PEG thioacetate (PEG TAc). PEG MME was dried using a Dean Stark trap, and 2.5 eq of thionyl bromide was added. The reaction was then refluxed for 4 h at 140° C. The toluene was evaporated, and the polymer was dissolved in dichloromethane (DCM) and precipitated in cold diethyl ether. The final conversion was accomplished by dissolving the PEG-Br in dimethylformamide (DMF) with 5 eq $K_2CO_3$ and 5 eq thiolacetic acid, and stirring overnight. The product was filtered, and the DMF was evaporated and dissolved in DCM. The PEG-TAc was purified over activated charcoal and precipitated in cold diethyl ether.

The present invention provides various block copolymers having at least two blocks, one hydrophilic and one hydrophobic. Block copolymers may further include additional blocks, be interrupted with hydrolysable chemical moieties, or be otherwise modified. Each block of the copolymer is important for self-assembly and biological function. The size of each block may be determined independently of the other blocks, e.g., to tailor the function of each block. Each block may be synthesized and bound to the other blocks using methods known in the art, e.g., as described in US 2003/0059906 and WO 2007/008300, which are hereby incorporated by reference.

Block Copolymers

Hydrophilic Blocks.

The hydrophilic block, e.g., PEG, may be utilized to (i) prevent non-specific nucleic acid/positively charged polymer complex interactions with serum proteins, cells, and tissues in the body, which allows for specific interactions to be designed via incorporated ligands, and (ii) increase the solubility of the complexes in aqueous milieu.

Polymers or molecules that are soluble or swell in an aqueous environment will prevent protein absorption while still enhancing the solubility of the particles. For example, carbohydrate polymers such as hyaluronic acid (HA) may swell to about 1000 times their volume and are used in nature to prevent protein absorption. Other carbohydrate polymer or molecule candidates are found in nature. Exemplary hydrophilic blocks include poly(ethylene glycol), poly(ethylene oxide)-co-poly(propylene oxide) di- or multiblock copolymers, poly(ethylene oxide), poly(vinyl alcohol), poly(ethylene-co-vinyl alcohol), poly(N-vinyl pyrrolidone), poly(acrylic acid), poly(ethyloxazoline), poly(alkylacrylates), poly(acrylamide), poly(N-alkylacrylamides), polypeptides, polysaccharides, poly(N-acryloylmorpholine), or poly(N,N-dialkylacrylamides), potentially bearing polar, ionic, or ionizable groups in the aliphatic chains.

Hydrophilic blocks having molecular weights between 500 and 10,000 Da are practical and convenient, although higher molecular weight hydrophilic blocks may be employed. For hydrophilic blocks, a number of repeating units between about 10 and about 250 is preferable because of the ease with which these materials may be eliminated from the body by renal filtration. A PEG hydrophilic block is preferably between 750 and 5500 Da, e.g., between 2 and 5 kDa (e.g., a block containing 115 units). Hydrophilic blocks with a larger number of repeating units may also be cleared by the kidney but at slower rates than hydrophilic polymers of lower number of repeating units, which may place limits on doses that can be applied.

Hydrophobic Blocks.

The hydrophobic block may include any polymer that is hydrophobic in context. A preferred hydrophobic block is PPS. Poly(propylene glycol) (PPG), a structural homolog of PPS with an oxygen atom instead of a sulfur atom in the backbone, may also be employed. Larger PPG chains may be required relative to the useful length of PPS chains. In general, polymers that have low melting or glass transition temperatures are most desirable because this characteristic is most conducive to effective micellization.

Other polymers that are otherwise hydrophilic but are derivatized with hydrophobic functionalities on their side chains may be used in the hydrophobic block. Examples include esterified poly(acrylic acid), esterified poly(glutamic acid) or poly(aspartic acid), and hydrophobic peptides or peptoids (e.g., N-substituted glycines). Hydrophobic blocks having molecular weights between 300 and 5000 Da are practical and convenient, although higher molecular weight hydrophobic blocks may also be employed. For hydrophobic blocks, the number of repeating units is, for example, between about 4 and about 240, preferably between 4 and 70. For example, a polypropylene sulfide hydrophobic block can vary from 150 to 16,000 Da, e.g., from 200 to 15,000 Da, depending on the initial hydrophilic block (e.g., PEG) used and the desired application. A higher number of repeating units may also be utilized; however, self-assembled structures from such polymers may be far from their equilibrium morphology.

Additional Blocks.

In certain embodiments, the copolymers of the invention have only two polymeric blocks, although other chemical moieties, e.g., hydrolysable, charged, or biologically active moieties, may be present. In other embodiments, the copolymers may include three or more polymeric blocks. Such additional blocks may be employed, for example, (i) to bind nucleic acids or other charged molecules via electrostatic interactions, (ii) to help a self-assembled structure enter the cell, and/or (iii) to execute another biological function. When employed to bind charged molecules, e.g., a nucleic acid, the additional block is preferably sized to produce reversible binding with the charged molecule. For example, at least 10%, 20%, 30%, 40%, 50%, 60%, 70%, 80%, 90%, or even 95% of the charged molecule may dissociate from the block under appropriate cellular conditions, e.g., in the cytosol or within the nucleus. In addition, short blocks may be employed to reduce or eliminate any toxicity.

The use of a positively charged block in a block copolymer is particularly advantageous for the formation of small complexes with, e.g., nucleic acids. Exemplary positively charged blocks are a polypeptide (e.g., polylysine), poly(ethylene-imine) (PEI), poly(amidoamine), poly(sodium 1-(N-acryloylpiperazin-1-yl)diazen-1-ium-1,2-diolate), poly(sodium 1-(N-acryloylhomopiperazin-1-yl)diazen-1-ium-1,2-diolate) or poly(sodium 1-(N-acryloyl-2,5-dimethylpiperazin-1-yl)diazen-1-ium-1,2-diolate). Blocks having a positive charge between 5 and 20 at physiological pH are practical and convenient, although blocks with a larger number of positive charges may also be employed. Molecular weights of a positively charged block between 500 and 10000 Da are preferred. For polymers such as PEI, a number of repeating units between about 10 and about 250 is preferred. The longer a charged block becomes, in general the higher the corresponding cytotoxicity.

Additional blocks may also be peptides. Peptides have been extensively utilized in the field of pharmaceutical agent delivery and other medical applications owing to the multitude of chemical and biological functionalities they can embody. Examples of charged peptides include the biologically active TAT peptide and oligo(lysine) (e.g., $Lys_9$) peptides. Both peptides are charged and can bind to nucleic acids and other negatively charged molecules. Additional examples of charged blocks include oligo(histidine), oligo(arginine) (e.g., $Arg_9$), and copolymers of Lys, Arg, and His.

Furthermore, poly(amidoamine) (PAMAM) dendrimers have been used to complex nucleic acids and may be included in a charged block. PAMAM has been shown to efficiently escape the endosome, allowing release of the complexed contents in the cytosol.

Polymer Modifications.

Polymeric blocks in the copolymers of the invention may also be modified. Such modifications include adding charged groups (e.g., carboxylic acids groups, sulfates, sulfones, and amines), hydrophilic groups (e.g., hydroxyl), hydrophobic groups (e.g., phenyl or methyl), hydrolysable groups (e.g., ester, amide, thioester, anhydride, or ketal moieties), or groups sensitive to oxidation. In particular, portions of a polymeric block that are exposed to aqueous solution in supramolecular structures may be modified to include one or more charged groups to allow for more efficient uptake in vivo, as described herein. Blocks copolymers may also be end capped with various groups as described herein and known in the art.

One particular example of a block copolymer modified by a hydrolysable chemical moiety is illustrated in Example 1. For such a hydrolysable block copolymer, the PEG diacrylate preferably has a molecular weight from 200 to 600 Da. Other hydrolysable blocks that may be used include lactide or caprolactone groups.

Degradation In Vivo.

In order to avoid irreversible accumulation in the targeted organs, the self-assembled carriers may demonstrate some form of degradation in vivo. Polysulfides are known to readily undergo oxidation to polysulfoxides and even to polysulfones, e.g., by the action of mild oxidizing agents, such as hydrogen peroxide. Under biological conditions, this oxidation can be performed extracellularly, e.g., by macrophages, or intracellularly after cellular uptake into an endosomal or lysosomal compartment. A similar kind of reaction is used for oxidizing thioether-terminated PEGs (used as emulsifiers in pulp and paper processing) in order to break wastewater foams (see, e.g., U.S. Pat. No. 4,618,400).

The conversion of the polysulfides to polysulfoxides can solubilize the block copolymers in water, allowing elimination through excretion (Napoli A et al., Nature Materials, 2004. 3(3): p. 183-189). The conversion can trigger the instability of self-assembled aggregates, e.g., the conversion of gels to micelles or soluble polymers, the conversion of vesicles to micelles or soluble polymers, or the conversion of micelles into micelles of different size and shape or to soluble polymers. Destabilizing the aggregate can also trigger the release of any encapsulated pharmaceutical agents, e.g., a nucleic acid. The mechanisms of clearance of soluble polymers are relatively well understood. The most important such mechanism is clearance via renal filtration, the effective molecular weight cutoff of which is approximately 30,000. Particles of size less than approximately 100 nm can be cleared from the bloodstream in the liver. Lymphatic uptake also may play a role in clearance.

Copolymers of the invention may also be synthesized such that they respond to the changing environment of the endosome. For example, a disulfide bond may be introduced into the copolymer so that, as the environment of the endosome becomes reducing, the bond is cleaved, thereby destabilizing the complex within the endosome. An N—$PO_3$ bond, which responds to low pH, e.g., as in an endosome, may also be introduced into the structure. Additional bonds that are sensitive to intracellular degradation, such as vinyl ether, orthoester, and acyl hydrazone, may also be employed.

Copolymers of the invention may also be synthesized so that a hydrophobic or hydrophilic block is interrupted with a hydrolysable chemical moiety, e.g., an ester or amide. Hydrolysis of the moiety leads to a change in the relative amount of hydrophobic or hydrophilic block, which in turn can lead to destabilization of a supramolecular complex by changing its favorable self-assembled morphology. In one embodiment, the half-life of the hydrolysable bond is between 1 hour and 1 year in an aqueous solution at pH 7.4 and 37° C. Desirably, the half-life is between 1 day and 9 months, more preferably between 2 days and 6 months, and most preferably between 4 days and 3 weeks. In certain embodiments, a thioether or secondary amine is present at the alpha or beta position relative to the hydrolysable bond.

Self Assembly.

Amphiphilic block copolymers have long been used as surfactants and dispersants in a wide variety of applications; the formation of organized structures in a solvent that is selective for one of the blocks is the basis of this behavior.

Well-defined self-assembled structures, such as spherical or cylindrical micelles, lamellae, or vesicles (Booth et al., Macromol. Chem., Rapid Commun. 2000, 21, 501-527; Won, Science 1999, 283, 960-963; Discher et al., Science 1999, 284, 1143-1146; and Eisenberg et al., Macromolecules 1998, 31, 3509) have been observed in poly(oxyalkylene) block copolymers. The concentration of the polymer solution and the temperature greatly influence the kind of aggregates that can be formed: changing, e.g., from liquid spherical micellar phases to cubic phases of spherical micelles and finally to hexagonal phases of cylindrical micelles upon an increase in temperature (Mortensen, Progr. Coll. Polym. Sci. 1993, 93, 72-75). The phase diagram and accessible structures of the amphiphilic block copolymers exhibit a dependence on the block length and number, i.e., basically, on the hydrophilic/lipophilic balance.

Block copolymers of PEG with poly(ethylethylene) have shown a propensity to form worm-like micelles at a ratio 55/45 between hydrophilic and hydrophobic repeating units (total MW=4900), and to form lamellar structures at a ratio 40:37 (total MW=3900).

This invention provides materials capable of generating a wide variety of structures; for example, a material containing long sequences of hydrophilic groups is able to form micelles, while a high hydrophobic content facilitates the formation of lamellar gels, and, under suitable conditions, vesicles.

The formation of vesicles can also be achieved by adding to water a solution or colloidal suspension of the copolymer in an organic solvent and subsequently removing the organic solvent.

Combinations of two or more block copolymers of the invention may also be employed to form supramolecular structures. Typically, PEG-PPS with Mw fractions (REG) of approximately 0.99-0.7 form micelles, whereas Mw fractions (fPEG) of approximately 0.30 to 0.25 form vesicles.

Thermal Transitions of Block Copolymer Assemblies.

The invention also features a method of making micelles from vesicles. In these embodiments, micelles are formed from block copolymers that are thermodynamically disposed to form vesicles. Upon heating the micelles, they spontaneously form vesicles. When the micelles are in aqueous suspension with a dissolved compound, e.g., pharmaceutical agent, the process of forming vesicles results in encapsulation of the pharmaceutical agent in the interior of the vesicles.

For example, polymer micelles are formed using a polymer composition with an fPEG that thermodynamically favors vesicle formation. In suspension, the micelles are metastable and can be highly concentrated. Application of heat to the metastable micelles induces spontaneous formation of vesicles, which are very small and homogeneous in size distribution. Pharmaceutical agent incorporated in the micelle suspension is loaded within the vesicles during their formation. Micelles can be made from copolymers that would otherwise form vesicles, i.e., under nonequilibrium conditions, by means that include rapidly dissolving/dispersing the polymer without heating, for example from powdered or lyophilized polymer. This rapid dissolution kinetically traps the polymer in a micellar form. Addition of mobility provides the opportunity for the nonequilibrium form to approach equilibrium, here by forming the more favored vesicle morphology.

We have shown that when heat is applied to a mixture containing block copolymers and a salt, the mixture melts into a homogeneous composition. Small molecule pharmaceutical agents also melt in the formulation during heating. This process leads to encapsulation of the pharmaceutical agents in the supramolecular structures, e.g., micelles or vesicles, formed by the block copolymers.

Drying and Rehydrating Block Copolymer Assemblies.

Supramolecular structures of the invention, e.g., vesicles, may be dehydrated and made into dry formulations. Such dry formulations may be rehydrated in vivo upon administration or in vitro prior to administration or other use. Preferably, a dry formulation includes less than 5% water by weight. The limit of water content that is acceptable in a dry formulation may be determined by measurement of storage lifetime by standard methods. Dry formulations may be stable for greater than two weeks, one month, six months, or one year. A pharmaceutical agent encapsulated within the supramolecular structures, e.g., by a method described herein, may be reconstituted to an active form upon rehydration. The dried compositions may be rehydrated in any aqueous solution, e.g., in a pharmaceutically acceptable diluent. In conventional pharmaceutical processing by a number of drying methods, water contents substantially less than 5% may be easily reached.

Pharmaceutical Compositions.

In suitable conditions for the generation of micelles, e.g., by treatment with heat, the block copolymers of the invention can be used for the encapsulation of pharmaceutical agents such as peptides, nucleic acids, antibiotics (e.g., ampicillin or tetracycline), chemotherapeutics (e.g., doxorubicin), or other small molecule pharmaceutical agents. When lamellar phases are to be formed, vesicles can be generated from the lamellar structure bending; in this way, water-dissolved pharmaceutical agents can be entrapped in the internal cavity of the vesicle. Pharmaceutical compositions may also employ excipients that increase the encapsulation efficiency of one or more block copolymers for pharmaceutical agents that are hydrophilic, hydrophobic, or amphiphilic. The excipients may increase the compatibility of the pharmaceutical agent with one or more blocks in the block copolymer, e.g., by reducing repulsive forces or increasing attractive forces between the pharmaceutical agent and one or more blocks of the block copolymer.

Suitable exemplary excipients are 1,8-diazabicyclo[5.4.0] undec-7-ene (DBU) and polyethylene glycol (e.g., PEG 600). PEG having a molecular weight between 400 and 800 Da is effective as an excipient. Polyethylene glycols outside of this range have not been effective. Other excipients that may be used are PPS-PEG copolymers and hydrobromide or hydrochloride salts of common organic bases such as triethanolamine, triethylamine, or pyridine. The addition of an excipient to a mixture containing a block copolymer and a pharmaceutical agent may increase the efficiency of encapsulation of the pharmaceutical agent by greater than 1.5-fold, 3-fold, 5-fold, 10-fold, or 50-fold. Examples of improved pharmaceutical agent encapsulation in the presence of excipients are provided herein.

The copolymers of the invention may be dispersed in a pharmaceutically acceptable diluent. In addition, self-assembled structures of the invention may include pharmaceutical agents or biologically active compounds. In various embodiments, the pharmaceutical composition includes about 1 ng to about 20 mg of pharmaceutical agent, e.g., a nucleic acid or a hydrophobic compound (e.g., paclitaxel or dexamethasone). In some embodiments, the composition contains about 10 ng to about 10 mg, about 0.1 mg to about 500 mg, about 1 mg to about 350 mg, about 25 mg to about 250 mg, or about 100 mg of pharmaceutical agents. Those of skill in the art of clinical pharmacology can readily arrive at dosing amounts using routine experimentation.

Suitable diluents include, but are not limited to, saline, buffered saline, dextrose, water, glycerol, ethanol, and combinations thereof. The composition can be adapted for the mode of administration and can be in the form of, for example, a pill, tablet, capsule, spray, powder, or liquid. In some embodiments, the pharmaceutical composition contains one or more pharmaceutically acceptable additives suitable for the selected route and mode of administration. These compositions may be administered by, without limitation, any parenteral route including intravenous, intra-arterial, intramuscular, subcutaneous, intradermal, intraperitoneal, intrathecal, as well as topically, orally, and by mucosal routes of delivery such as intranasal, inhalation, rectal, vaginal, buccal, and sublingual. In some embodiments, the pharmaceutical compositions of the invention are prepared for administration to vertebrate (e.g., mammalian) subjects in the form of liquids, including sterile, non-pyrogenic liquids for injection, emulsions, powders, aerosols, tablets, capsules, enteric coated tablets, or suppositories. Conventional procedures and ingredients for the selection and preparation of suitable formulations are described, for example, in Remington's Pharmaceutical Sciences (2003-20th edition) and in The United States Pharmacopeia: The National Formulary (USP 24 NF19), published in 1999.

Pharmaceutical agents may be hydrophilic, hydrophobic, or amphoteric. The type of supramolecular structure employed to encapsulate an agent will depend on the solubility characteristics of the agent and the copolymer. Typically, hydrophilic agents will be encapsulated in the interior of vesicles, and hydrophobic agents will be encapsulated in the interior of micelles. Agents that may be employed with copolymers of the invention include but are not limited to natural and synthetic compounds, e.g., a nucleic acid, having the following therapeutic activities: anti-arthritic, anti-arrhythmic, anti-bacterial, anticholinergic, anticancer, anticoagulant, antidiuretic, antidote, antiepileptic, antifungal, anti-inflammatory, antimetabolic, antimigraine, antineoplastic, antiparasitic, antipyretic, antiseizure, antisera, antispasmodic, analgesic, anesthetic, beta-blocking, biological response modifying, bone metabolism regulating, cardiovascular, diuretic, enzymatic, fertility enhancing, growth-promoting, hemostatic, hormonal, hormonal suppressing, hypercalcemic alleviating, hypocalcemic alleviating, hypoglycemic alleviating, hyperglycemic alleviating, immunosuppressive, immunoenhancing, muscle relaxing, neurotransmitting, parasympathomimetic, sympathominetric plasma extending, plasma expanding, psychotropic, thrombolytic, chemotherapeutic, and vasodilating.

Nucleic Acids.

In certain embodiments of the invention, the block copolymer composition contains a nucleic acid. The nucleic acid may associate with one or more blocks of a copolymer and may be incorporated into supramolecular structures containing block copolymers, e.g., micelles or vesicles. In preferred embodiments, the nucleic acid is present in a therapeutically effective amount in a pharmaceutical composition containing one or more block copolymers. Antisense oligonucleotides, small interfering RNAs (siRNAs), aptamers, and plasmid DNA are examples.

Oligonucleotides containing modified backbones or non-natural internucleoside linkages may be employed. Nucleobase oligomers that have modified oligonucleotide backbones include, for example, phosphorothioates, chiral phosphorothioates, phosphorodithioates, phosphotriesters, aminoalkyl-phosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity, wherein the adjacent pairs of nucleoside units are linked 3'-5' to 5'-3' or 2'-5' to 5'-2'. Various salts, mixed salts and free acid forms are also included. Representative United States patents that teach the preparation of the above phosphorus-containing linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; and 5,625,050, each of which is herein incorporated by reference.

Nucleobase oligomers having modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ components. Representative United States patents that teach the preparation of the above oligonucleotides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439, each of which is herein incorporated by reference.

In other nucleobase oligomers, both the sugar and the internucleoside linkage, i.e., the backbone, are replaced with novel groups. One such nucleobase oligomer, is referred to as a Peptide Nucleic Acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Methods for making and using these nucleobase oligomers are described, for example, in "Peptide Nucleic Acids: Protocols and Applications" Ed. P. E. Nielsen, Horizon Press, Norfolk, United Kingdom, 1999. Representative United States patents that teach the preparation of PNAs include, but are not limited to, U.S. Pat. Nos. 5,539,082; 5,714,331; and 5,719,262, each of which is herein incorporated by reference. Further teaching of PNA compounds can be found in Nielsen et al., Science, 1991, 254, 1497-1500.

In particular embodiments of the invention, the nucleobase oligomers have phosphorothioate backbones and nucleosides with heteroatom backbones, and in particular —$CH_2$—NH—O—$CH_2$—, —$CH_2$—N($CH_3$)—O—$CH_2$— (known as a methylene (methylimino) or MMI backbone), —$CH_2$—O—N($CH_3$)—$CH_2$—, —$CH_2$—N($CH_3$)—N($CH_3$)—$CH_2$—, and —O—N($CH_3$)—$CH_2$—$CH_2$—. In other embodiments, the oligonucleotides have morpholino backbone structures described in U.S. Pat. No. 5,034,506.

Nucleobase oligomers may also contain one or more substituted sugar moieties. Nucleobase oligomers comprise one of the following at the 2' position: OH; F; O—, S—, or N-alkyl; O—, S—, or N-alkenyl; O-, S- or N-alkynyl; or O-alkyl-O-alkyl, wherein the alkyl, alkenyl, and alkynyl may be substituted or unsubstituted $C_1$ to $C_{10}$ alkyl or $C_2$ to $C_{10}$ alkenyl and alkynyl. Particularly preferred are $O[(CH_2)_nO]_mCH_3$, $O(CH_2)_nOCH_3$, $O(CH_2)_nNH_2$, $O(CH_2)_nCH_3$, $O(CH_2)_nONH_2$, and $O(CH_2)_nON[(CH_2)_nCH_3)]_2$, where n and m are from 1 to about 10. Other preferred nucleobase oligomers include one of the following at the 2' position: $C_1$ to $C_{10}$ lower alkyl, substituted lower alkyl, alkaryl, aralkyl, O-alkaryl, or O-aralkyl, SH, $SCH_3$, OCN, Cl, Br, CN, $CF_3$, $OCF_3$, $SOCH_3$, $SO_2CH_3$, $ONO_2$, $NO_2$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of a nucleobase oligomer, a group for improving the pharmacodynamic properties of a nucleobase oligomer, or other substituents having similar properties. Preferred modifications are 2'-O-methyl and 2'-methoxyethoxy (2'-O—$CH_2CH_2OCH_3$, also known as 2'-O-(2-methoxyethyl) or 2'-MOE). Another desirable modification is 2'-dimethylaminooxyethoxy (i.e., $O(CH_2)_2ON(CH_3)_2$), also known as 2'-DMAOE. Other modifications include, 2'-aminopropoxy (2'-$OCH_2CH_2CH_2NH_2$) and 2'-fluoro (2'-F). Similar modifications may also be made at other positions on an oligonucleotide or other nucleobase oligomer, particularly the 3' position of the sugar of the 3' terminal nucleotide or in 2'-5' linked oligonucleotides and the 5' position of the 5' terminal nucleotide. Nucleobase oligomers may also have sugar mimetics such as cyclobutyl moieties in place of the pentofuranosyl sugar. Representative United States patents that teach the preparation of such modified sugar structures include, but are not limited to, U.S. Pat. Nos. 4,981,957, 5,118,800, 5,319,080, 5,359,044, 5,393,878, 5,446,137, 5,466,786, 5,514,785, 5,519,134, 5,567,811, 5,576,427, 5,591,722, 5,597,909, 5,610,300, 5,627,053, 5,639,873, 5,646,265, 5,658,873, 5,670,633, and 5,700,920, each of which is herein incorporated by reference in its entirety.

Nucleobase oligomers may also include nucleobase modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases, such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine, 2-thiocytosine, 5-halouracil, cytosine, 5-propynyl uracil, 6-azo uracil, thymine, 5-uracil (pseudouracil), 4-thiouracil, 8-halo, 8-amino, 8-thiol, 8-thioalkyl, 8-hydroxyl and other 8-substituted adenines and guanines, 5-halo (e.g., 5-bromo), 5-trifluoromethyl and other 5-substituted uracils and cytosines, 7-methylguanine, 7-methyladenine, 8-azaguanine, 8-azaadenine, 7-deazaguanine, 7-deazaadenine, and 3-deazaguanine and 3-deazaadenine. Further nucleobases include those disclosed in U.S. Pat. No. 3,687,808, those disclosed in The Concise Encyclopedia of Polymer Science and Engineering, pages 858-859, Kroschwitz, J. I., ed. John Wiley & Sons, 1990, those disclosed by Englisch et al., Angewandte Chemie, International Edition, 1991, 30, 613, and those disclosed by Sanghvi, Y. S., Chapter 15, Antisense Research and Applications, pages 289-302, Crooke, S. T. and Lebleu, B., ed., CRC Press, 1993. Certain of these nucleobases are particularly useful for increasing the binding affinity of an antisense or (partially) complementary oligonucleotide of the invention to a target nucleic acid. These include 5-substituted pyrimidines, 6-azapyrimidines, and N-2, N-6, and O-6 substituted purines, including 2-aminopropyladenine, 5-propynyluracil and 5-propynylcytosine. 5-methylcytosine substitutions have been shown to increase nucleic acid duplex stability by 0.6-1.2° C. (Sanghvi, Y. S., Crooke, S. T. and Lebleu, B., eds., Antisense Research and Applications, CRC Press, Boca Raton, 1993, pp. 276-278) and are desirable base substitutions, even more particularly when combined with 2'-O-methoxyethyl or 2'-O-methyl sugar modifications. Representative United States patents that teach the preparation of certain of the above-noted modified nucleobases as well as other modified nucleobases include U.S. Pat. Nos. 4,845,205, 5,130,302, 5,134,066, 5,175,273, 5,367,066, 5,432,272, 5,457,187, 5,459,255, 5,484,908, 5,502,177, 5,525,711, 5,552,540, 5,587,469, 5,594,121, 5,596,091, 5,614,617, 5,681,941, and 5,750,692, each of which is herein incorporated by reference.

Another modification of a nucleobase oligomer of the invention involves chemically linking to the nucleobase oligomer one or more moieties or conjugates that enhance the activity, cellular distribution, or cellular uptake of the oligonucleotide. Such moieties include but are not limited to lipid moieties such as a cholesterol moiety (Letsinger et al., Proc. Natl. Acad. Sci. USA, 86:6553-6556, 1989), cholic acid (Manoharan et al., Bioorg. Med. Chem. Let, 4:1053-1060, 1994), a thioether, e.g., hexyl-5-tritylthiol (Manoharan et al., Ann. N.Y. Acad. Sci., 660:306-309, 1992 Manoharan et al., Bioorg. Med. Chem. Let., 3:2765-2770, 1993), a thiocholesterol (Oberhauser et al., Nucl. Acids Res., 20:533-538, 1992), an aliphatic chain, e.g., dodecandiol or undecyl residues (Saison-Behmoaras et al., EMBO J., 10:1111-1118, 1991; Kabanov et al., FEBS Lett., 259:327-330, 1990; Svinarchuk et al., Biochimie, 75:49-54, 1993), a phospholipid, e.g., di-hexadecyl-rac-glycerol or triethylammonium 1,2-di-O-hexadecyl-rac-glycero-3-H-phosphonate (Manoharan et al., Tetrahedron Lett., 36:3651-3654, 1995; Shea et al., Nucl. Acids Res., 18:3777-3783, 1990), a polyamine or a polyethylene glycol chain (Manoharan et al., Nucleosides & Nucleotides, 14:969-973, 1995), or adamantane acetic acid (Manoharan et al., Tetrahedron Lett., 36:3651-3654, 1995), a palmityl moiety (Mishra et al., Biochim. Biophys. Acta, 1264:229-237, 1995), or an octadecylamine or hexylamino-carbonyl-oxycholesterol moiety (Crooke et al., J. Pharmacol. Exp. Ther., 277:923-937, 1996). Representative United States patents that teach the preparation of such nucleobase oligomer conjugates include U.S. Pat. Nos. 4,587,044, 4,605,735, 4,667,025, 4,762,779, 4,789,737, 4,824,941, 4,828,979, 4,835,263, 4,876,335, 4,904,582, 4,948,882, 4,958,013, 5,082,830, 5,109,124, 5,112,963, 5,118,802, 5,138,045, 5,214,136, 5,218,105, 5,245,022, 5,254,469, 5,258,506, 5,262,536, 5,272,250, 5,292,873, 5,317,098, 5,371,241, 5,391,723, 5,414,077, 5,416,203, 5,451,463, 5,486,603, 5,510,475, 5,512,439, 5,512,667, 5,514,785, 5,525,465, 5,541,313, 5,545,730, 5,552,538, 5,565,552, 5,567,810, 5,574,142, 5,578,717, 5,578,718, 5,580,731, 5,585,481, 5,587,371, 5,591,584, 5,595,726, 5,597,696, 5,599,923, 5,599,928, 5,608,046, and 5,688,941, each of which is herein incorporated by reference.

The present invention also includes nucleobase oligomers that are chimeric compounds. "Chimeric" nucleobase oligomers are nucleobase oligomers, particularly oligonucleotides, that contain two or more chemically distinct regions, each made up of at least one monomer unit, i.e., a nucleotide in the case of an oligonucleotide. A chimeric nucleobase oligomer may contain one or more regions to confer increased resistance to nuclease degradation, increased cellular uptake, and/or increased binding affinity for the target nucleic acid.

Chimeric nucleobase oligomers may be formed as composite structures of two or more nucleobase oligomers as described above. Such nucleobase oligomers, when oligonucleotides, have also been referred to in the art as hybrids or gapmers. Representative United States patents that teach the preparation of such hybrid structures include U.S. Pat. Nos. 5,013,830, 5,149,797, 5,220,007, 5,256,775, 5,366,878, 5,403,711, 5,491,133, 5,565,350, 5,623,065, 5,652,355, 5,652,356, and 5,700,922, each of which is herein incorporated by reference in its entirety.

Locked nucleic acids (LNAs) are nucleobase oligomers that can be employed in the present invention. LNAs contain a 2'O, 4'-C methylene bridge that restrict the flexibility of the ribofuranose ring of the nucleotide analog and locks it into the rigid bicyclic N-type conformation. LNAs show improved resistance to certain exo- and endonucleases and activate RNAse H, and can be incorporated into almost any nucleobase oligomer. Moreover, LNA-containing nucleobase oligomers can be prepared using standard phosphoramidite synthesis protocols. Additional details regarding LNAs can be found in PCT publication No. WO 99/14226 and U.S. Patent Application Publication No. US 2002/0094555 A1, each of which is hereby incorporated by reference.

Arabinonucleic acids (ANAs) can also be employed in the present invention. ANAs are nucleobase oligomers based on D-arabinose sugars instead of the natural D-2'-deoxyribose sugars. Underivatized ANA analogs have similar binding affinity for RNA as do phosphorothioates. When the arabinose sugar is derivatized with fluorine (2' F-ANA), an enhancement in binding affinity results, and selective hydrolysis of bound RNA occurs efficiently in the resulting ANA/RNA and F-ANA/RNA duplexes. These analogs can be made stable in cellular media by a derivatization at their termini with simple L sugars. The use of ANAs in therapy is discussed, for example, in Damha et al., Nucleosides Nucleotides & Nucleic Acids 20: 429-440, 2001.

Polypeptides

Polypeptides may be employed in embodiments of the invention. The amino acids of the polypeptide may be natural, non-natural, or a mixture thereof. The polypeptide may be produced by recombinant genetic technology or chemical synthesis using methods known in the art. Examples of polypeptides are a single-chain peptide fragment (e.g., a polypeptide of 5-20 amino acids joined by conventional peptide bonds), a naturally occurring protein, and an antibody or antigen-binding fragment thereof.

Methods for Internalization and Therapeutic Methods

The copolymers may utilize biological pathways for both delivery and therapeutic action. In one embodiment, a block copolymer that self-assembles in aqueous environments into nanoscale micelles or vesicles may be employed for the delivery of pharmaceutical agents, such as siRNA or other nucleic acids. Moreover, a block copolymer of the invention can exploit changing intracellular environments, e.g., the reductive environment of the endosome, for efficient delivery of the pharmaceutical agent and a biological pathway for therapeutic action, e.g., the activation of the RNAi pathway for gene silencing. The development of biologically responsive materials to induce release of a therapeutic agent within the early endosome and destabilize it holds promise for the development of delivery systems that can overcome limitations of current delivery systems.

Colloidal particles such as nanospheres, liposomes, and micelles have been studied extensively for site-specific pharmaceutical agent delivery. Unless the reticuloendothelial system (RES) is a target, the particles must escape capture by the RES of the liver and the filtration activity of the lungs. Prolonged survival of colloidal systems in the blood has been obtained by the use of PEG-containing amphiphiles (Lasic et al., Ed. Stealth Liposomes; CRC Press: Boca Raton, Fla., 1995). By virtue of marked reduction of opsonization by plasma proteins, the macrophages clearance of PEG-based liposomes has been drastically reduced (Torchilin et al., Biochim Biophys Acta 1994, 1195, 11-20).

A variety of internalization agents, i.e., compounds or species that enhance the internalization of the copolymers of the invention, such as antibodies, growth factors, cytokines, adhesion factors, oligonucleotide sequences and nuclear localization sequences has served to enhance the delivery capabilities of PEG-coated liposomes, and it has been demonstrated that the maximal activity is shown by ligands tethered to the distal end of PEG chains (Blume et al., Biochim. Biophys. Acta 1993, 1149, 180-184; Zalipsky et al., Bioconjugate Chem. 1995, 6, 705-708; Zalipsky, J. Controlled Release 1996, 39, 153-161; Gabizon, Bioconjugate Chem. 1999, 10, 289-298). This approach can be employed with the polymers of the invention. Some internalization agents can lead to very efficient cellular uptake, such as the use of growth factors, for example, fibroblast growth factor to effect cellular uptake of DNA formulations. Other internalization agents can lead to very efficient intracellular trafficking, such as nuclear localization sequences, and these may be used in the present invention. Additional internalization agents include transferrin, folate, a lectin, growth factor, an RGD peptide, and a mannose-containing glycopeptide.

The copolymers of the present invention are useful for any application in the controlled release, e.g., in the cytosol or nucleus, of a pharmaceutical agent, e.g., nucleic acid. The release of the contents, e.g., the nucleic acid, of the self-assembled aggregate, such as a micelle or vesicle, may be achieved through sensitivity of the aggregate to the environment, such as triggering a release based on the lowering of pH, increase in the extent of oxidation, and increase in the concentration of proteases during the process of intracellular trafficking from the endosome to the lysosome. Excipients may also be incorporated along with the pharmaceutical agent to help it in reaching its final biological target, such as incorporation of agents that assist in destabilizing or permeabilizing biological membranes, such as the endosomal or lysosomal membranes, to enhance transport of the nucleic acid into the cytoplasm or ultimately into the nucleus.

The polymers may also be employed to deliver mixtures of pharmaceutical agents, e.g., two or more different nucleic acids or a nucleic acid and a pharmaceutical agent, such as an antibiotic.

Gene-Based Pharmaceutical Agents.

The block copolymers of the invention may be used to deliver nucleic acids for the up- or down-regulation of genes. Examples of nucleic acids include siRNA, ODN (antisense), and pDNA, including pDNA encoding therapeutic proteins.

The internalization of DNA/positively charged polymer complexes can be enhanced by the covalent attachment of ligands, such as transferrin, folate, lectins, epidermal growth factor (EGF), RGD peptides, and mannose-containing species such as mannose-containing glycopeptides to bind to the mannose receptor (Kircheis, R., et al., Gene Ther, 1997. 4(5): p. 409-18; Gottschalk, S., et al., Gene Ther, 1994. 1(3): p. 185-91; Erbacher, P., et al., Hum Gene Ther, 1996. 7(6): p. 721-9; Blessing, T., et al., Bioconjug Chem, 2001. 12(4): p. 529-37; Harbottle, R. P., et al., Hum Gene Ther, 1998. 9(7): p. 1037-47; East L, Isacke C M. Biochimica et Biophysica Acta, 2002 1572: p. 364-386). The ligand functions to direct the DNA complex to the cell surface by specifically binding to a receptor, and mediating endocytosis. Fusogenic peptides and other functional groups have been attached to enhance endosomal escape of the DNA complex (Carlisle, R. C., Curr Opin Mol Ther, 2002. 4(4): p. 306-12; Bell, P. C., et al., J Am Chem Soc, 2003. 125(6): p. 1551-8).

There exists a parallel need for delivery of other gene-based pharmaceutical agents, including ODN and pDNA. Here, the agent must also be delivered to the cell and its cytoplasm, and eventually to the nucleus. With ODNs, the need is even more acute, since they function by stoichiometric competition. With plasmids, the challenge is even higher, since the large size of the plasmid greatly inhibits its passage through the membranes of the cell, e.g., the plasma membrane and the endosomal membranes.

Methods for Delivering Pharmaceutical Agents.

The invention provides methods for delivering a pharmaceutical agent, e.g., a nucleic acid, to a cell or an animal, e.g., a mammal, or plant by contacting the cell or administering to the animal a pharmaceutical composition of the invention. The delivery may reduce or inhibit the expression of a target gene in a cell (e.g., a eukaryotic cell, a plant cell, an animal cell, an invertebrate cell, a vertebrate cell, such as a mammalian or human cell, or a pathogen cell) or may treat the animal or cell by any mechanism specific to the pharmaceutical agent contained in the pharmaceutical composition. The method may be used to treat infection by a pathogen or to treat a nonpathogenic disease, e.g., cancer, postsurgical adhesions, scar formation, or restenosis after removal of arterial block (e.g., via balloon angioplasty or stenting). Typically, a nucleic acid internalized in the cell specifically reduces or inhibits the expression of a target gene, e.g., one associated with the disease (e.g., all or a region of a gene, a gene promoter, or a portion of a gene and its promoter). Exemplary pathogens include bacteria, protozoan, yeast, and fungi. In some embodiments, the nucleic acid or other molecule inhibits the expression of an endogenous gene in a vertebrate cell or a pathogen cell (e.g., a bacterial, a yeast cell, or a fungal cell), or inhibits the expression of a pathogen gene in a cell infected with the pathogen (e.g., a plant or animal cell). The nucleic acid or other molecule may also reduce or inhibit the expression of an endogenous gene, e.g., in a cancer cell or in cells that produce undesirable effects, e.g., restenosis, scar formation, and postsurgical adhesions. In some embodiments, the target gene is a gene associated with cancer, such as an oncogene, or a gene encoding a protein associated with a disease, such as a mutant protein, a dominant negative protein, or an overexpressed protein.

Alternatively, the nucleic acid or other pharmaceutical agent delivered may increase the expression of a gene. For example, the copolymer of the invention may be used to deliver a plasmid or other gene vector to the nucleus where one or more genes contained on the plasmid may be expressed. Such a system may be employed to enable expression of gene products that are not expressed endogenously, to increase expression of endogenous gene products, and to replace gene products that are mutated or otherwise non-functional. In some cases, local expression of these genes is mostly desired, as with, without limitation, vascular endothelial growth factor, transforming growth factor beta, platelet derived growth factor, fibroblast growth factor, insulin-like growth factor, bone morphogenetic protein, growth and differentiation factor, nerve growth factor, neurotrophin, cytokines, and transcription factors, such as hif-1alpha, runx2, and sox-9.

The nucleic acid or other pharmaceutical agent may reduce, inhibit, or increase expression of a target gene by at least 20, 40, 60, 80, 90, 95, or 100%. The methods of the invention may also be used to simultaneously reduce or inhibit the expression of one or more target genes while increasing the expression of one or more other target genes.

Treatment of Disease.

The compositions of the inventions may be used to treat a disease, e.g., cancer, in an animal, e.g., a human. Exemplary cancers that can be treated using the methods described herein include prostate cancers, breast cancers, ovarian cancers, pancreatic cancers, gastric cancers, bladder cancers, salivary gland carcinomas, gastrointestinal cancers, lung cancers, colon cancers, melanomas, brain tumors, leukemias, lymphomas, and carcinomas. Benign tumors may also be treated or prevented using the methods of the present invention. Other cancers and cancer related genes that may be targeted are known in the art.

Exemplary endogenous proteins that may be associated with disease include ANA (anti-nuclear antibody) found in SLE (systemic lupus erythematosis), abnormal immunoglobulins including IgG and IgA, Bence Jones protein associated with various multiple myelomas, and abnormal amyloid proteins in various amyloidoses including hereditary amyloidosis and Alzheimer's disease. In Huntington's Disease, a genetic abnormality in the HD (huntingtin) gene results in an expanded tract of repeated glutamine residues. In addition to this mutant gene, HD patients have a copy of chromosome 4 which has a normal sized CAG repeat. Thus, methods of the invention can be used to silence the abnormal gene, but not the normal gene.

Exemplary diseases that may be treated with the methods include infection by pathogens, such as a virus, a bacterium, a yeast, a fungus, a protozoan, or a parasite. The nucleic acid may be delivered to the pathogen or to a cell infected with the pathogen. The pathogen may be an intracellular or extracellular pathogen. The target nucleic acid sequence is, for example, a gene of the pathogen that is necessary for replication and/or pathogenesis, or a gene encoding a cellular receptor necessary for a cell to be infected with the pathogen. Such methods may be employed prior to, concurrent with, or following the administration of the in-dwelling device to a patient to prevent infections. In-dwelling devices include, but are not limited to, surgical implants, prosthetic devices, and catheters, i.e., devices that are introduced to the body of an individual and remain in position for an extended time. Such devices include, for example, artificial joints, heart valves, pacemakers, vascular grafts, vascular catheters, cerebrospinal fluid shunts, urinary catheters, and continuous ambulatory peritoneal dialysis (CAPD) catheters.

A bacterial infection may be due to one or more of the following bacteria: *Chlamydophila pneumoniae, C. psittaci, C. abortus, Chlamydia trachomatis, Simkania negevensis, Parachlamydia acanthamoebae, Pseudomonas aeruginosa, P. alcaligenes, P. chlororaphis, P. fluorescens, P. luteola, P. mendocina, P. monteilii, P. oryzihabitans, P. pertocinogena, P. pseudalcaligenes, P. putida, P. stutzeri, Burkholderia cepacia, Aeromonas hydrophilia, Escherichia coli, Citrobacter freundii, Salmonella typhimurium, S. typhi, S. paratyphi, S. enteritidis, Shigella dysenteriae, S. flexneri, S. sonnei, Enterobacter cloacae, E. aerogenes, Klebsiella pneumoniae, K oxytoca, Serratia marcescens, Francisella tularensis, Morganella morganii, Proteus mirabilis, Proteus vulgaris, Providencia alcalifaciens, P. rettgeri, P. stuartii, Acinetobacter calcoaceticus, A. haemolyticus, Yersinia enterocolitica, Y pestis, Y. pseudotuberculosis, Y. intermedia, Bordetella pertussis, B. parapertussis, B. bronchiseptica, Haemophilus influenzae, H. parainfluenzae, H. haemolyticus, H. parahaemolyticus, H. ducreyi, Pasteurella multocida, P. haemolytica, Branhamella catarrhalis, Helicobacter pylori, Campylobacter fetus, C. jejuni, C. coli, Borrelia burgdorferi, V. cholerae, V. parahaemolyticus, Legionella pneumophila, Listeria monocytogenes, Neisseria gonorrhea, N. meningitidis, Kingella dentrificans, K kingae, K oralis, Moraxella catarrhalis, M atlantae, M lacunata, M nonliquefaciens, M osloensis, M phenylpyruvica, Gardnerella vaginalis, Bacteroides fragilis, Bacteroides distasonis, Bacteroides 3452A homology group, Bacteroides vulgatus, B. ovalus, B. thetaiotaomicron, B. uniformis, B. eggerthii, B. splanchnicus, Clostridium difficile, Mycobacterium tuberculosis, M avium, M intracellulare, M leprae, C. diphtheriae, C. ulcerans, C. accolens, C. afermentans, C. amycolatum, C. argentorense, C. auris, C. bovis, C. confusum, C. coyleae, C. durum, C. falsenii, C. glucuronolyticum, C. imitans, C. jeikeium, C. kutscheri, C. kroppenstedtii, C. lipophilum, C. macginleyi, C. matruchoti, C. mucifaciens, C. pilosum, C. propinquum, C. renale, C. riegelii, C. sanguinis, C. singulare, C. striatum, C. sundsvallense, C. thomssenii, C. urealyticum, C. xerosis, Streptococcus pneumoniae, S. agalactiae, S. pyogenes, Enterococcus avium, E. casseliflavus, E. cecorum, E. dispar, E. durans, E. faecalis, E. faecium, E. flavescens, E. gallinarum, E. hirae, E. malodoratus, E. mundtii, E. pseudoavium, E. raffinosus, E. solitarius, Staphylococcus aureus, S. epidermidis, S. saprophyticus, S. intermedius, S. hyicus, S. haemolyticus, S. hominis,* and/or *S. saccharolyticus.*

A viral infection may be due to one or more of the following viruses: Hepatitis B, Hepatitis C, picornarirus, polio, HIV, coxsacchie, herpes simplex virus Type 1 and 2, St. Louis encephalitis, Epstein-Barr, myxoviruses, JC, coxsakieviruses B, togaviruses, measles, paramyxoviruses, echoviruses, bunyaviruses, cytomegaloviruses, varicella-zoster, mumps, equine encephalitis, lymphocytic choriomeningitis, rhabodoviruses including rabies, simian virus 40, human polyoma virus, parvoviruses, papilloma viruses, primate adenoviruses, coronaviruses, retroviruses, Dengue, yellow fever, Japanese encephalitis virus, BK, Retrovirus, Herpesvirus, Hepadenovirus, Poxvirus, Parvovirus, Papillornavirus, and Papovavirus. The target viral nucleic acid sequence is, for example, necessary for replication and/or pathogenesis of the virus in an infected cell. Such viral target genes are necessary for the propagation of the virus and include, e.g., the HIV gag, env, and pol genes, the HPV6 LI and E2 genes, the HPV I I LI and E2 genes, the HPV 16 E6 and E7 genes, the BPV 18 E6 and E7 genes, the HBV surface antigens, the HBV core antigen, HBV reverse transcriptase, the HSV gD gene, the HSVvp 16 gene, the HSV gC, gH, gL and gB genes, the HSV ICPO, ICP4 and ICP6 genes, Varicella zoster gB, gC and gH genes, and the BCR-abl chromosomal sequences, and non-coding viral polynucleotide sequences which provide regulatory functions necessary for transfer of the infection from cell to cell, e.g., the HIV LTR, and other viral promoter sequences, such as HSV vp 16 promoter, HSV-ICPO promoter, HSV-ICP4, ICP6 and gD promoters, the HBV surface antigen promoter, the HBV pre-genomic promoter, among others.

The copolymers of the invention can be used to treat subjects already infected with a virus, such as HIV, in order to shut down or inhibit a viral gene function essential to virus replication and/or pathogenesis, such as HIV gag. Alternatively, this method can be employed to inhibit the functions of viruses, which exist in mammals as latent viruses, e.g., Varicella zoster virus, the causative agent of shingles. Similarly, diseases such as atherosclerosis, ulcers, chronic fatigue syndrome, and autoimmune disorders, recurrences of HSV-I and HSV-2, HPV persistent infection, e.g., genital warts, and chronic BBV infection among others, which have been shown to be caused, at least in part, by viruses, bacteria, or another pathogen, can be treated according to this method by targeting certain viral polynucleotide sequences essential to viral replication and/or pathogenesis in the mammalian subject.

Preferably, the nucleic acid or other molecule is administered in an amount sufficient to treat the disease or condition, e.g., to prevent, stabilize, or inhibit the growth of the pathogen or to kill the pathogen or to increase or decrease the expression of an endogenous gene whose under- or overexpression results in a disease.

EXAMPLES

Example 1

Block Copolymer Functionality can be Designed to Enable Hydrolytic and Oxidative Sensitivity PPS serves as a useful hydrophobic block in micelle and vesicle formation, as it can be oxidized to form the hydrophilic sulfone and sulfoxide products, after which it can presumably be excreted from the body by renal filtration. It is possible to build into the block copolymeric amphiphile other degradable segments, for example hydrolyzable chemical moieties. Such moieties may be placed within the hydrophilic domain of the block copolymer, so that moieties' accessibility to water does not become a limiting factor in hydrolysis rate and thus release rate. One route by which to accomplish this is shown in FIG. 1.

Figure 1B:
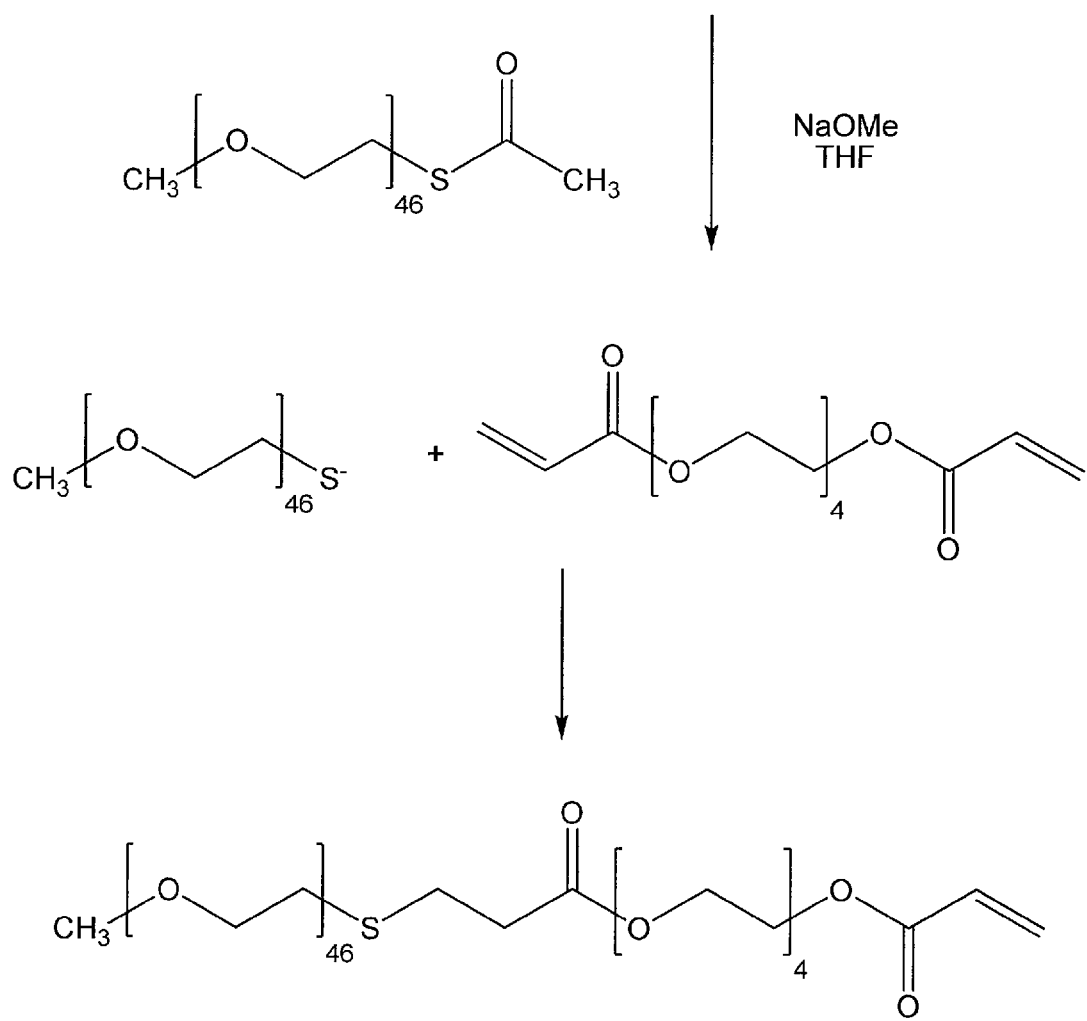
FIG. 1B. PEG-TAc was converted to PEG-ester-$EG_4$-acrylate by reacting PEG-TAc with PEG(200) diacrylate in excess. PEG-TAc was dissolved in tetrahydrofuran (THF) and degassed thoroughly. Next, the solution was added to 50 eq of PEG diacrylate in THF with 1 eq of triethylamine as base. The reaction was stirred overnight and purified by precipitation twice in cold diethyl ether.
Figure 1C:
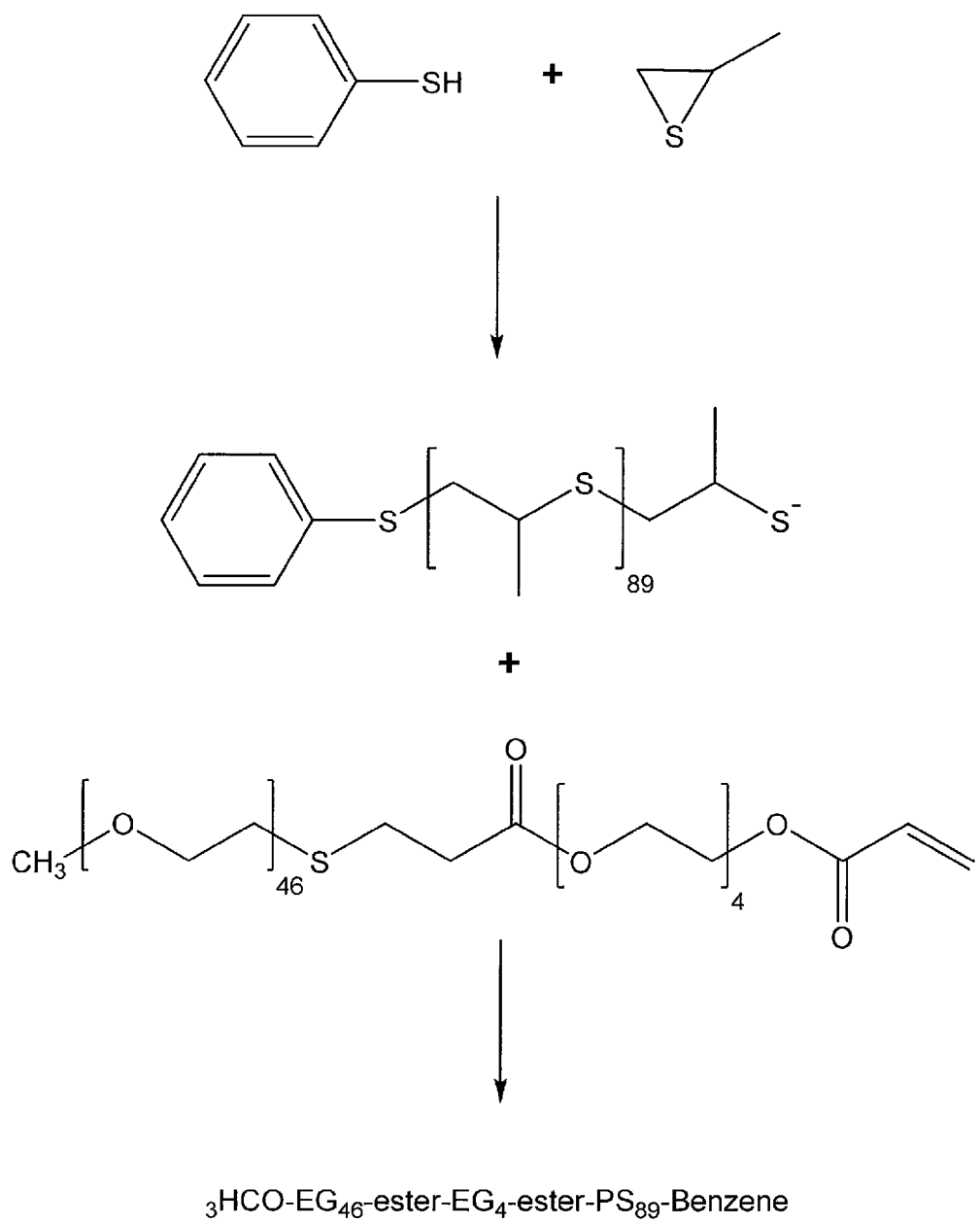
FIG. 1C. The final polymer was synthesized by forming the PPS block initiated from benzenethiol, and using the PEG-acrylate monomer as an end-capping reagent. This was accomplished by dissolving DBU base into THF and degassing. The benzenethiol was added under argon flow, and propylene sulfide monomer was added through a gastight septum. After 1 hr, the PEG-ester-$EG_4$-ester-acrylate was added, dissolved in THF, and degassed (0.5 eq). The reaction was allowed to stir overnight. The final product was purified by dissolving the dried mixture in toluene and filtering. After evaporating the toluene, the polymer was dissolved in DCM and precipitated in cold diethyl ether.
Figure 2:
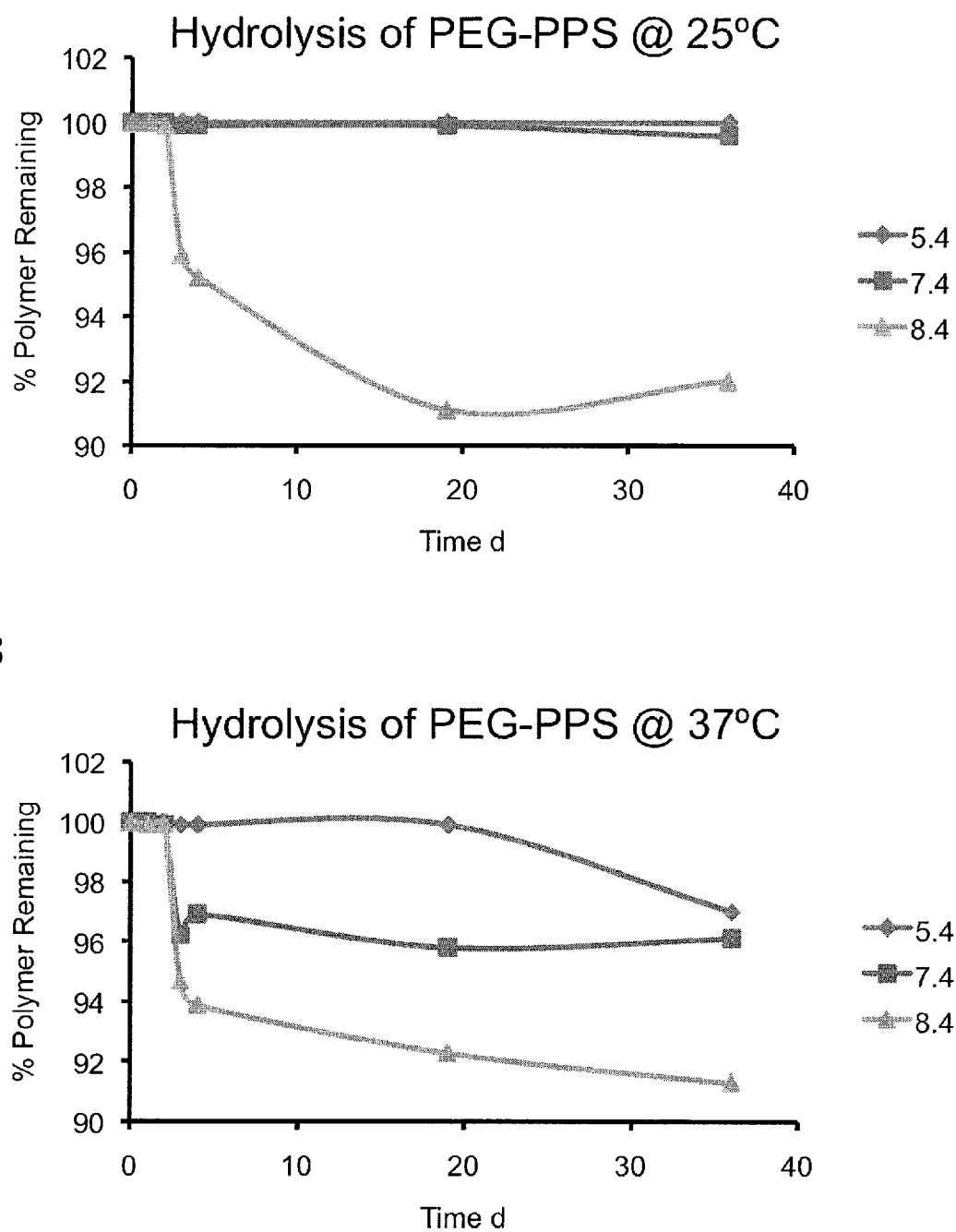
FIG. 2A. Hydrolysis of PEG-PPS at 25° C. over time at various pH values. The polymer was prepared by solvent dispersion from THF. The THF was removed under vacuum prior to the start of the study. Degradation was quantified via gel permeation chromatography, and the peaks for the free PPS and PEG blocks were quantified. At elevated pH (8.4) degradation occurred more rapidly, whereas at pH 5.4 no degredation was observed.
FIG. 2B. Degradation of the same polymer preparation as that shown in FIG. 2A was quantified at 37° C. Degradation was greatest at high pH owing to rapid hydrolysis of the ester bonds under these conditions. Unexpectedly, after 20 days degradation was also observed at pH 5.4.

The effect of the synthesis shown in FIG. 1 is to insert a hydrolytic link within the PEG chain, from which a PEG-PPS block copolymer is made, i.e., the PEG block is interrupted with a hydrolysable chemical moiety. As hydrolysis ensues, the fraction of the block copolymer comprised by the hydrophile ($f_{PEG}$) changes dramatically, thus changing the nature of the assembly that forms, releasing the contents of a vesicle, for example, formed from the block copolymer. This instability is illustrated in FIG. 2.

Example 2

Figure 4:
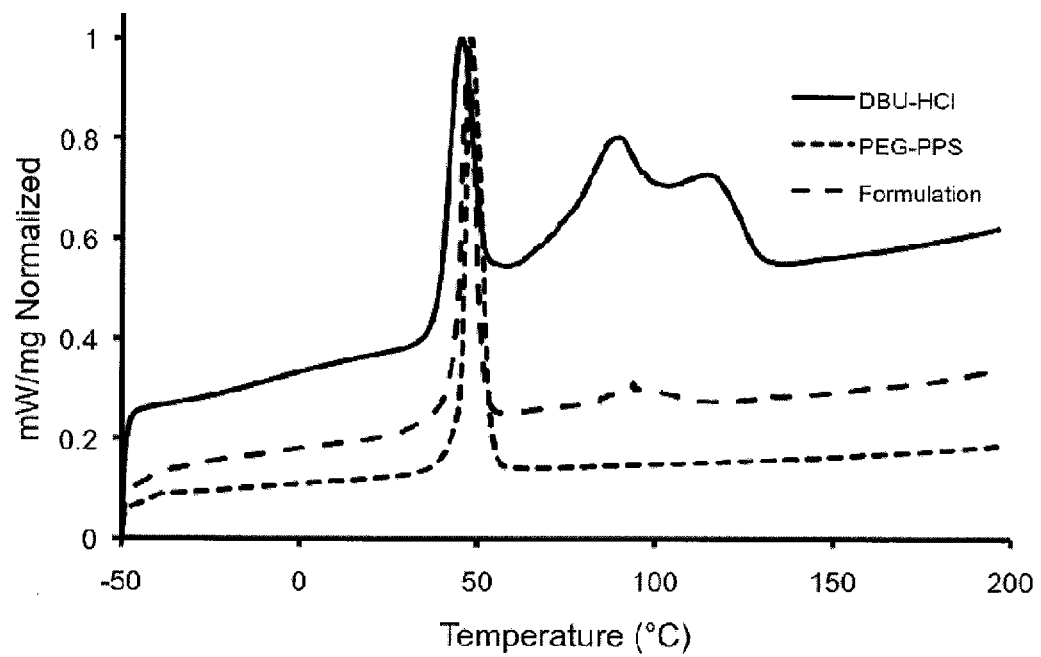
FIG. 4. Dynamic scanning calorimetry of PEG-PPS blended with DBU-HCl. The polymer and salt melted together creating a homogeneous blend of the two materials.
Figure 5:
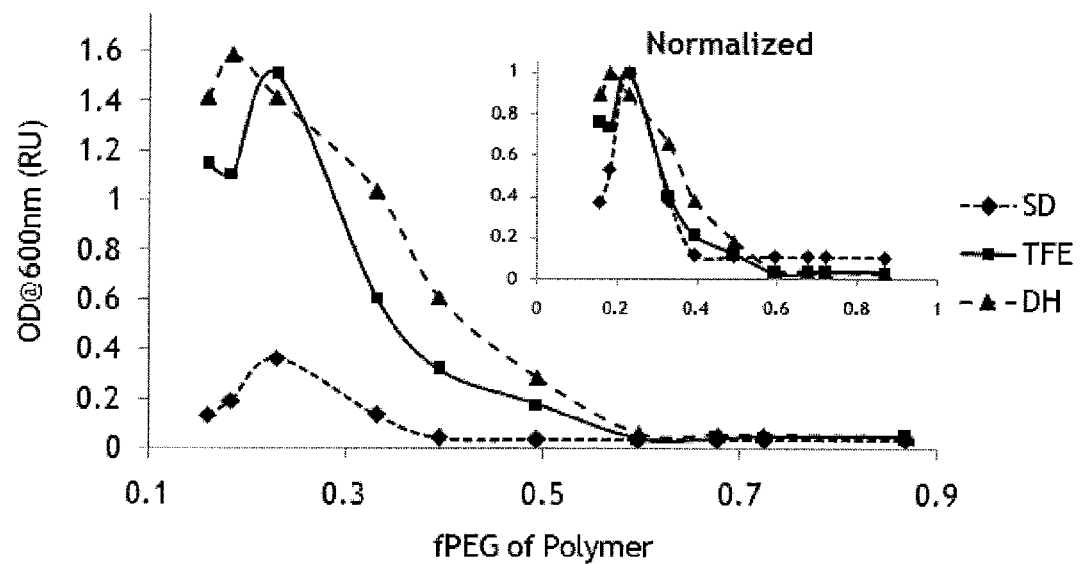
FIG. 5. Characterization of PEG-PPS processing methods using optical density. Samples were analyzed directly after preparation at the same concentration (5 mg/mL). Legend represents solvent dispersion (SD), thin film extrusion (TFE), and direct hydration (DH).
Figure 6:
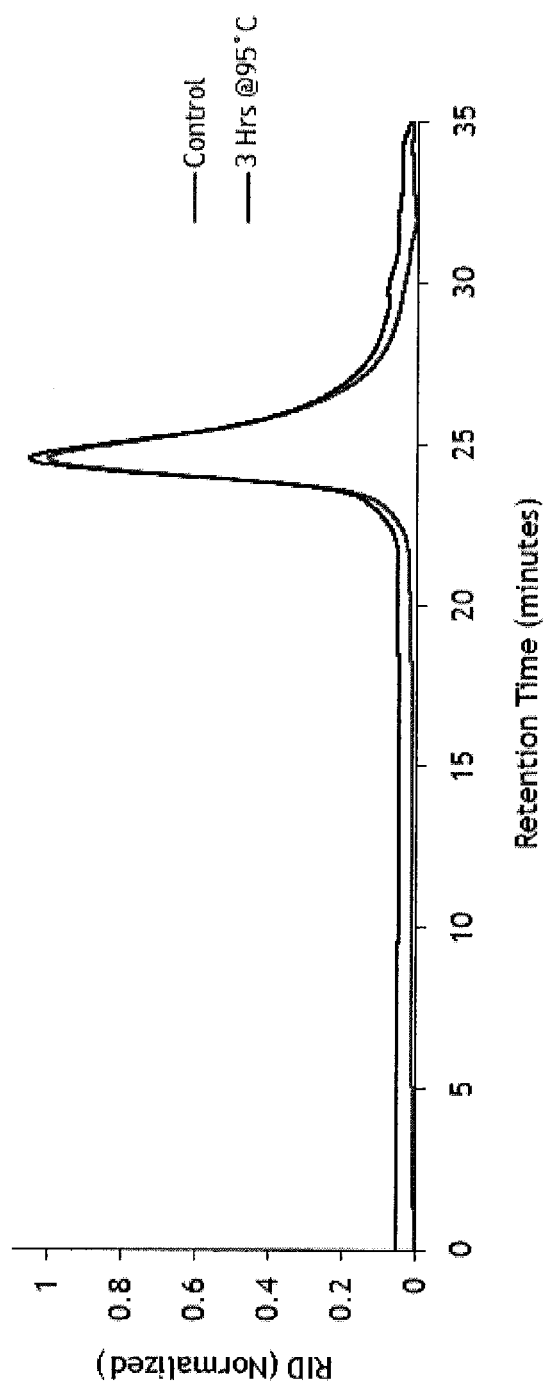
FIG. 6. Gel permeation chromatograph of a formulation incubated at 95° C. for three hours versus control. The data were acquired using a refractive index detector. For clarity, the control is shown on the bottom, and the 180 min sample is offset by 5%. Both chromatograms were normalized.
Figure 7:
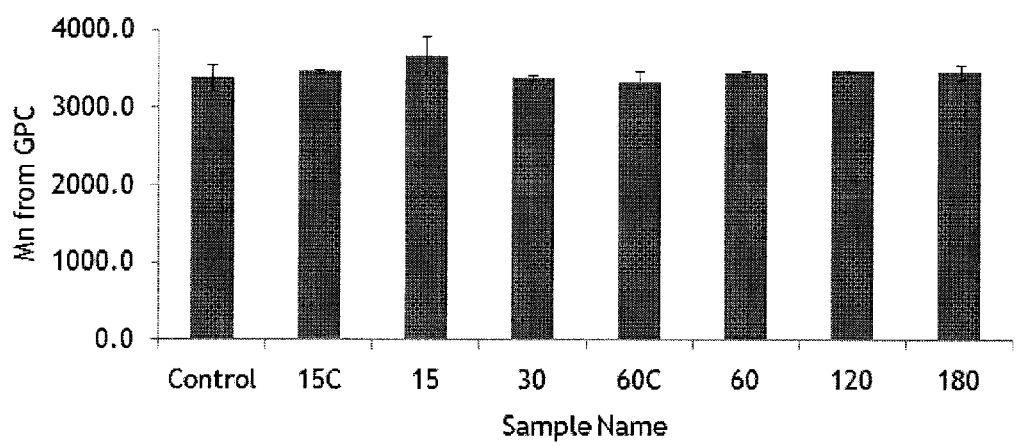
FIG. 7. Degradation study of PEG-PPS at 95° C. over time. The bar graph represents the average number average molecular weight (Mn) of the injected samples. From left to right are unheated polymer control (Control); 15 min control heated without salt (15 C); 15 and 30 min heated with salt (15, 30); 60 min heated without salt (60 C); 60, 120, and 180 min heated with salt (60, 120, 180). Student's t-test comparing the unheated control with the 180 min at 95° C. revealed the difference was not statistically significant. Mp represents peak molecular weight, and Mw represents weight average molecular weight. The PDI using gel permeation chromatography (GPC) is calculated by Mw/Mn. The Mn=Sum (NiMi)/Sum (Ni), and Mw=Sum (NiMi$^2$)/Sum (NiMi).
Figure 8:
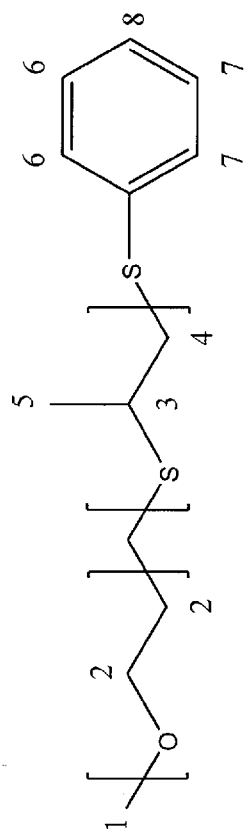
FIG. 8. Degradation study analyzed using proton NMR. Unheated, heated, and heated with salt preparations using the polymer $EG_{46}$-$PS_{12}$ were compared. The polymer and salt with polymer samples were heated at 95° C. for three hours prior to extraction in THF and precipitation in diethyl ether. The purified fractions were measured via proton-NMR in chloroform-D containing 0.1% TMS as an internal standard.
Figure 9:
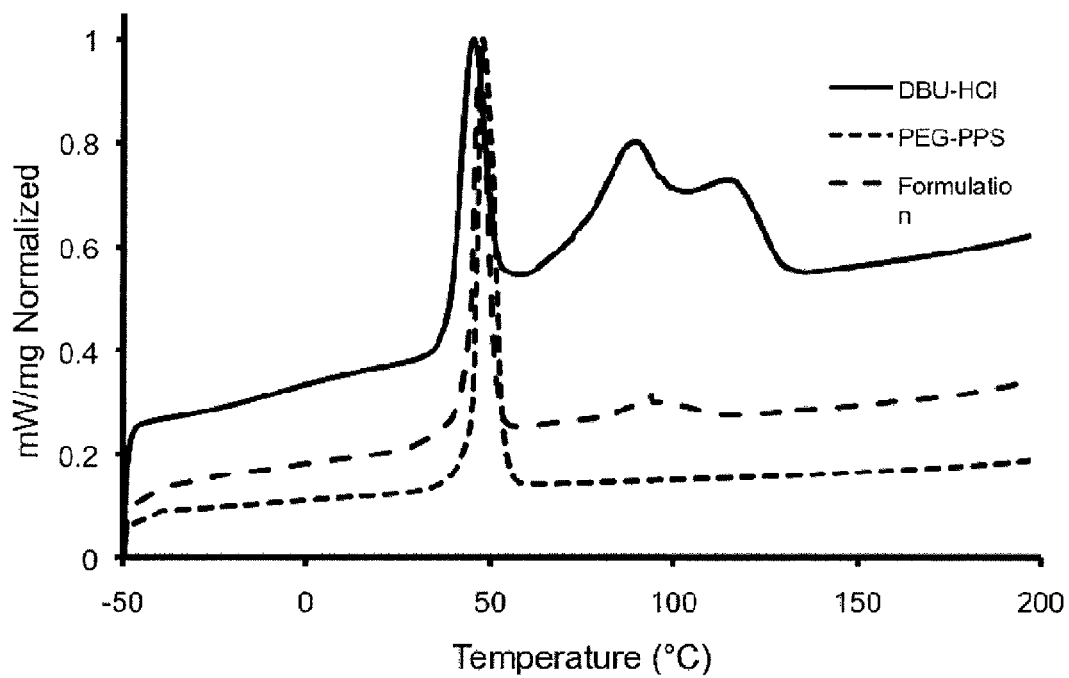
FIG. 9. Dynamic scanning calorimetry of the constituents separately and mixed together. The mixture was prepared by mixing $EG_{46}$-$PS_{12}$ 50/50 wt/wt with DBU-HCl and heating at 95° C. for 60 min. Samples were mixed thoroughly and measured on the DSC. For comparison, the polymer and DBU-HCl salt were also measured separately. The salt and polymer dissolved into a molten state upon heating.
Figure 10:
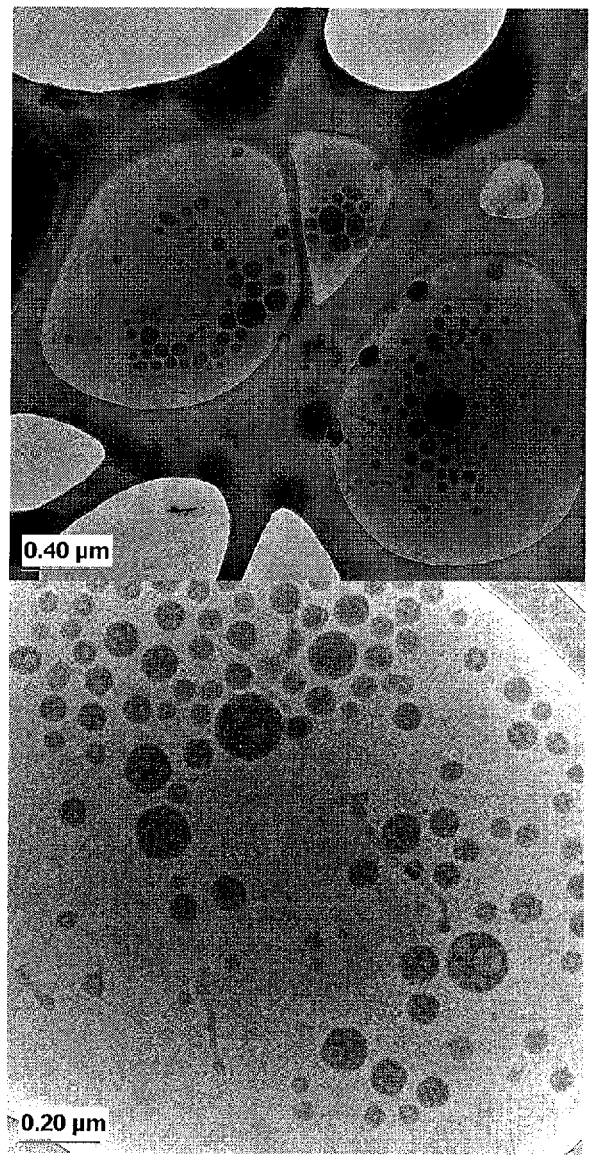
FIG. 10. Imaging vesicles formed via direct hydration using cryogenic TEM. The formed lamellar phases were vitrified on a holey carbon grid prior to imaging. Aggregates were extruded prior to analysis using cryo-TEM.
Figure 12:
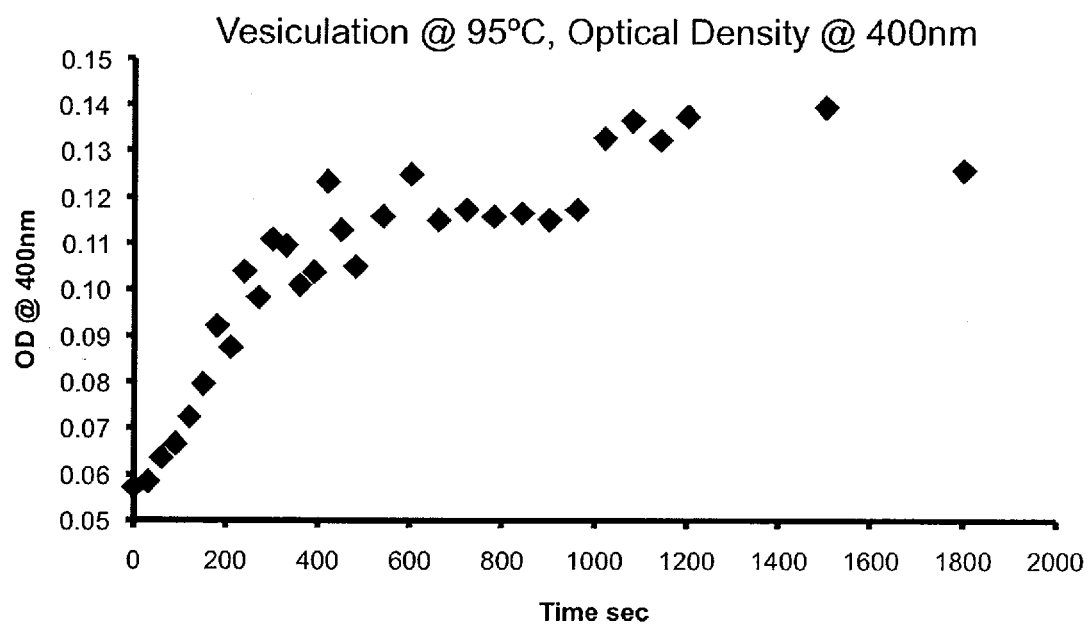
FIG. 12. Optical density change over time with heating of the polymer at 95° C. PEG-PPS ($EG_{46}$-$PS_{64}$) micelles were prepared from solvent dispersion in water using THF. After removing the THF under vacuum for 1 h, the suspension at 10 mg/mL was placed 1 mL each into 1.5 mL eppendorf tubes. To this aliquot, 200 µL of THF was added. Initial samples for time=0 optical density (OD) and dynamic light scattering (DLS) were removed, and the tubes were placed into a pre-heated incubator at 95° C. Samples were drawn at specific time points, 100 µl per sample and aliquoted into a 96 well plate on ice. After the final sample was removed, 50 µl of each sample was added to a new 96 well plate, and the optical density was measured at 400 nm using a plate reader in absorbance mode.
Figure 13:
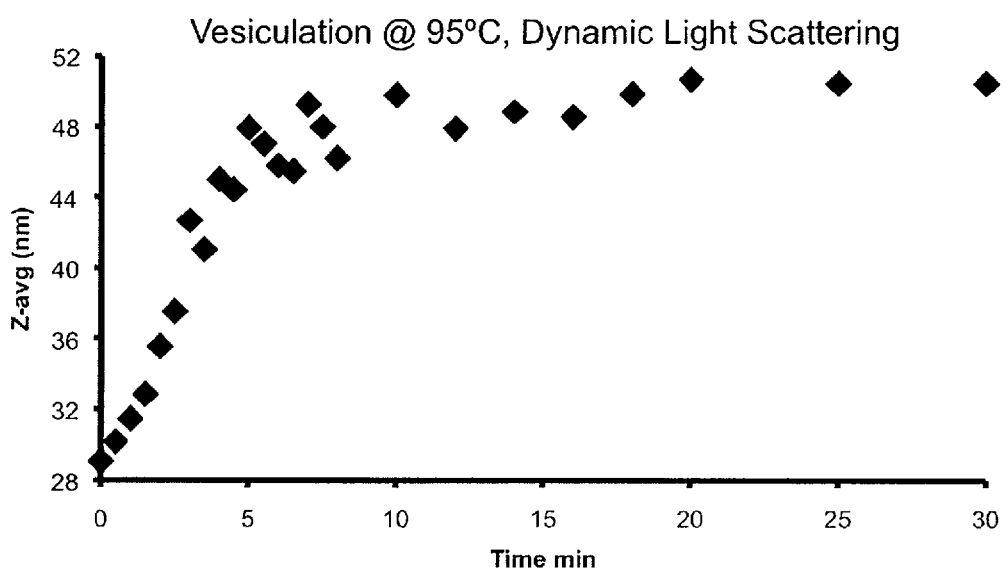
FIG. 13. The samples for optical density (50 µl) were dispersed into 550 µl of double distilled water and measured using DLS. Both the OD and DLS data clearly display a trend towards larger particle size, and changing morphology.
Figure 14:
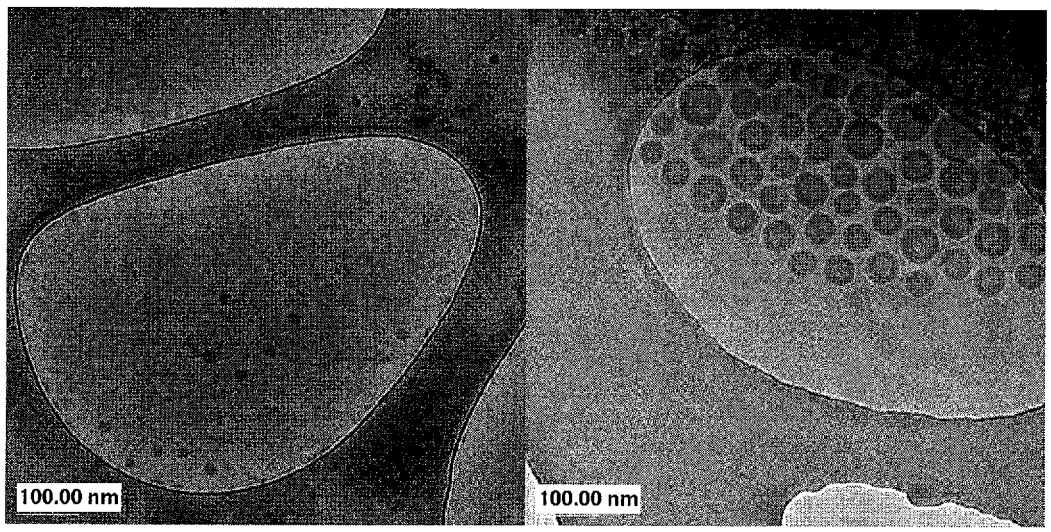
FIG. 14. Cryogenic Transmission Electron Microscopy of the thermal transition of PEG-PPS micelles into vesicles. The micelle sample (left) displays small aggregates of PEG-PPS in good agreement with the DLS results from FIG. 2. The 30 min sample (right) shows the vesicles (polymersomes) created during heating.
Figure 15:
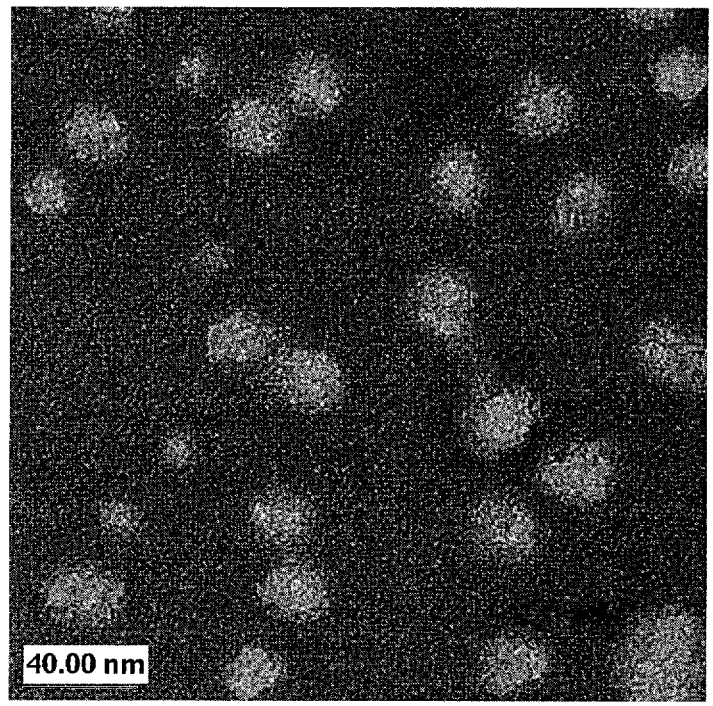
FIG. 15. The aggregation of PEG-PPS micelles during heating captured using negative staining TEM. Here the 3 min sample from the heating experiment was added to a 400 mesh carbon coated copper grid which had been prepared by glow discharge. The sample was then blotted off after 60 sec, and stained 30 sec with 2% uranyl acetate. The image above was taken at 75,000×. The 2-D surface vesicles form slowly into short worm like micelles.

Excipients can be Used to Enhance Encapsulation Efficiency of Hydrophobic Pharmaceutical Agents in Micelles Encapsulation of hydrophobic molecules within polymer micelles during micellization can be a difficult challenge. We have demonstrated a novel method for formation of polymer micelles that involves the use of an excipient in the encapsulation process that is both soluble in the polymer and soluble in water, considering the organic base DBU and the polymer PEG as examples, as shown in FIG. 3. FIG. 4, with Tables 1 and 2, demonstrate that the excipients can be used to obtain very high encapsulation efficiency of agents for which encapsulation is difficult, using paclitaxel and dexamethasone as examples.

TABLE 1

| Excipient | Pharmaceutical agent | Z-Avg (nm) | Volume (nm) | PDI |
|---|---|---|---|---|
| PEG600 | Paclitaxel | 66.36 | 24.54 | 0.292 |
| DBU-HCl | Paclitaxel | 52.02 | 22.55 | 0.610 |

TABLE 1-continued

| Excipient | Pharmaceutical agent | Z-Avg (nm) | Volume (nm) | PDI |
|---|---|---|---|---|
| PEG600 | Dexamethasone | 48.59 | 19.26 | 0.440 |
| DBU-HCl | Dexamethasone | 29.79 | 20.67 | 0.295 |

Dynamic Light Scattering of pharmaceutical agent loaded PEG-PPS micelles. 100 µl of sample was dispersed into 900 µl of distilled water before performing the DLS measurement. PDI represents the polydispersity index. PDI for DLS measurements is defined in ISO 13321:1996. The PDI is a dimensionless parameter defined as the broadness of the size distribution, which is defined as:

$$PDI = \frac{\mu_2}{(\Gamma)^2}$$

Where $\mu_2$ is the second cumulant and $\Gamma$ is the decay rate. In this case, the decay rate is representative of the Gaussian distribution of decay rates observed in the sample.

TABLE 2

Encapsulation efficiency (EE) of small molecule pharmaceutical agents using excipient formulations.

| Excipient | Pharmaceutical agent | EE |
|---|---|---|
| None | Dexamethasone | 5.5% |
| PEG600 | Paclitaxel | 75.9% |
| DBU-HCl | Paclitaxel | 40.6% |
| PEG600 | Dexamethasone | 37.7% |
| DBU-HCl | Dexamethasone | 46.1% |

Samples used in Table 2 were prepared as follows. 10 mg of PEG-PPS was added to a 1.5 mL centrifuge tube with either 90 mg of PEG600 or DBU-HCl, and 2 mg of either paclitaxel or dexamethasone. This was heated at 95° C. for 15 min and mixed thoroughly. After cooling to RT, the blend was slowly diluted to 1 mL with distilled water. The free pharmaceutical agent was pelleted via centrifugation for 10 minutes at 10,000 g, and the pellet and supernatant were separately freeze dried, and analyzed in THF via gel permeation chromatography. Dexamethasone and paclitaxel results were quantified using a standard curve.

Dexamethasone and amphotericin B were more efficiently encapsulated via solvent dispersion than via the method of the invention. In contrast, paclitaxel was more efficiently encapsulated via the method of the invention. Other pharmaceutical agents such as sirolimus and everolimus were also efficiently encapsulated using the methods of the invention. The encapsulation efficiency depends on the structure of the pharmaceutical agent. The flexibility of the PEG-PPS system to encapsulate pharmaceutical agents is very large because the system accommodates a variety of techniques to encapsulate most pharmaceutical agents at high efficiencies.

Example 3

Excipients can be Used to Enhance Encapsulation Efficiency of Hydrophilic Pharmaceutical Agents in Vesicles Polymeric vesicles represent very powerful tools for protection and delivery of hydrophilic pharmaceutical agents, such as peptides, proteins, nucleic acids, and genes; however, they are difficult to load. We have developed novel mechanisms to load vesicles at very high loading efficiency. One method is to dissolve in the polymer an excipient that is soluble both in the polymer and in water, such as DBU or PEGs, as illustrated above in the formation of polymer micelles. An aqueous solution of the pharmaceutical agent to be encapsulated is added to the polymer mixture with the excipient (the so-called direct hydration method). Typical results are illustrated in Table 3 and FIGS. 5-11.

TABLE 3

Particle size determination using dynamic light scattering.

| fPEG | SD | TFE | DH | DHE |
|------|------|------|--------|-------|
| 0.16 | 83.3 | 240.8 | 416.8 | 281.0 |
| 0.18 | 74.9 | 224.3 | 531.8 | 227.8 |
| 0.23 | 121.9 | 230.3 | 1417.0 | 125.5 |
| 0.33 | 102.9 | 196.4 | 458.3 | 139.4 |
| 0.39 | 43.4 | 315.7 | 695.4 | 117.7 |
| 0.49 | 20.0 | 159.4 | 278.6 | 97.8 |
| 0.60 | 15.9 | 46.5 | 113.6 | 46.4 |
| 0.68 | 18.4 | 55.5 | 244.3 | 77.5 |
| 0.72 | 25.2 | 42.7 | 225.1 | 83.6 |
| 0.87 | 14.6 | 56.4 | 558.4 | 114.0 |

Values are reported as zeta-size. The processing methods are solvent dispersion using tetrahydrofuran (SD), thin film extrusion (TFE), direct hydration (DH), and direct hydration with extrusion (DHE).

Example 4

Thermal Transitions can Induce Vesicle Formation from Micelles

As mentioned above, vesicles are powerful tools with which to encapsulate hydrophilic pharmaceutical agents, to modulate their release, to target their release, and to protect them from biological clearance and degradation mechanisms. We have developed a method to form polymer micelles involving application of heat. Polymer micelles are formed, using a polymer composition with an fPEG that would thermodynamically form vesicles instead. In suspension, the micelles can be metastable and can be concentrated to a high degree. Application of heat to the metastable micelles induces spontaneous formation of vesicles, which can be very small and homogeneous in size distribution. Pharmaceutical agent incorporated in the micelle suspension will be loaded within the vesicles during their formation. The approach is illustrated in FIGS. 12-15.

The ultrasmall size of the polymer vesicles formed by this method may be particularly useful in some applications. For example, in targeting tumors from the bloodstream via the enhanced permeation and retention effect, smaller particles are more effective than larger particles in penetration of the fenestrated endothelium in the tumor microcirculation. Smaller particles are more effective than larger ones in penetration of the arterial wall under physiological pressure or mild overpressure, in penetration of mucosal surfaces and targeting cells beneath, such as dendritic cells, in permeation of the interstitium to target lymph nodes draining the tissue site, and in targeting the lymphatics in the gut.

Example 5

PEG-PPS Vesicle Formulations can be Stable Upon Drying and Rehydration

Figure 16:
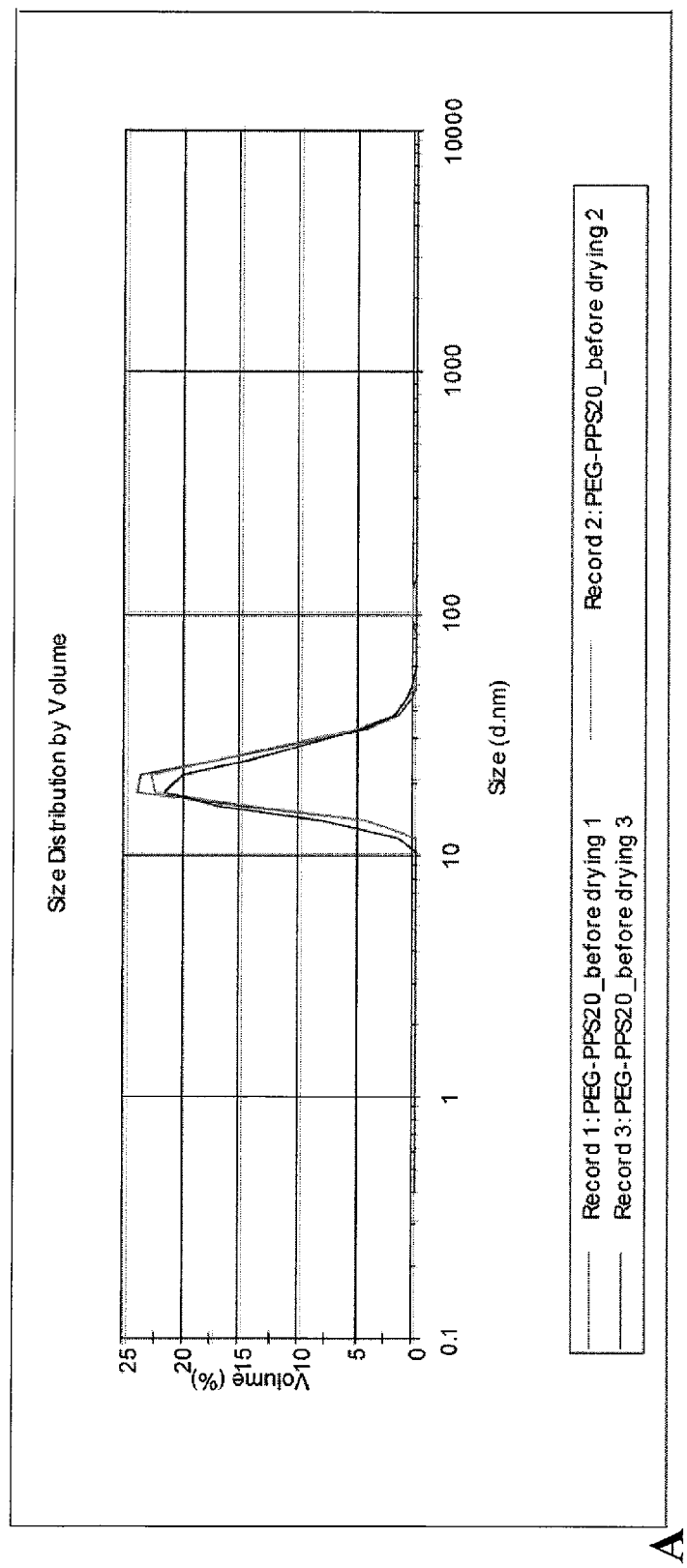
FIG. 16A. Particle size distribution by dynamic light scattering of PEG44-PPS20 cyclosporine A-loaded polymer micelles.
FIG. 16B. Particle size distribution of the micelles of FIG. 16A after drying and rehydration.
Figure 16:
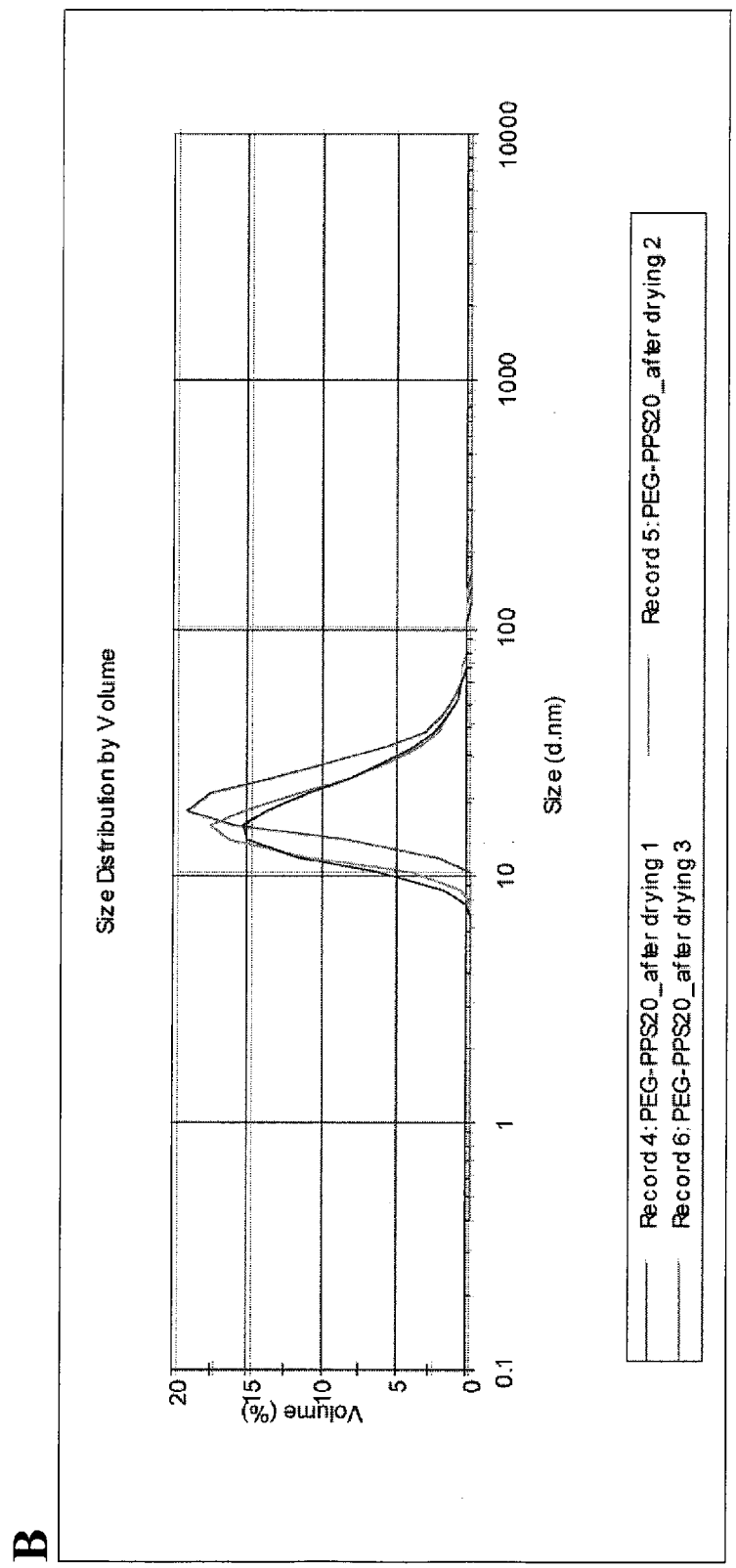
Figure 17A:
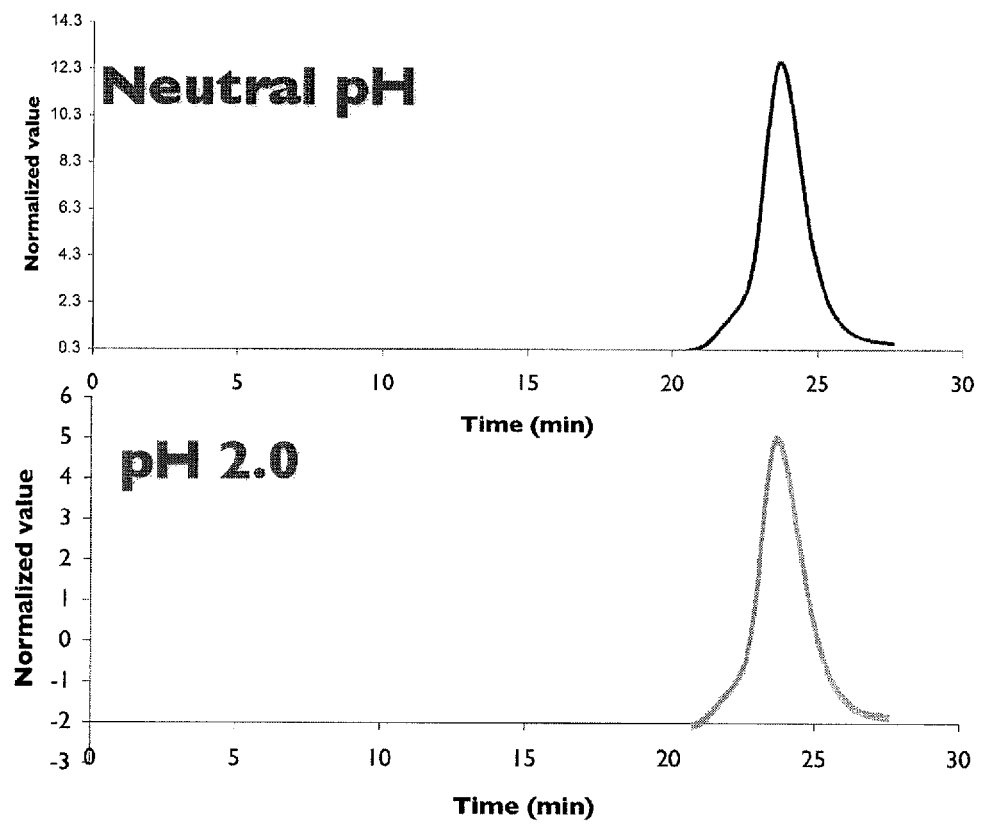
FIG. 17A. Stability of $PEG_{44}$-$PPS_{20}$ after exposure to gastric pH, as measured by gel permeation chromatography.
Figure 17B:
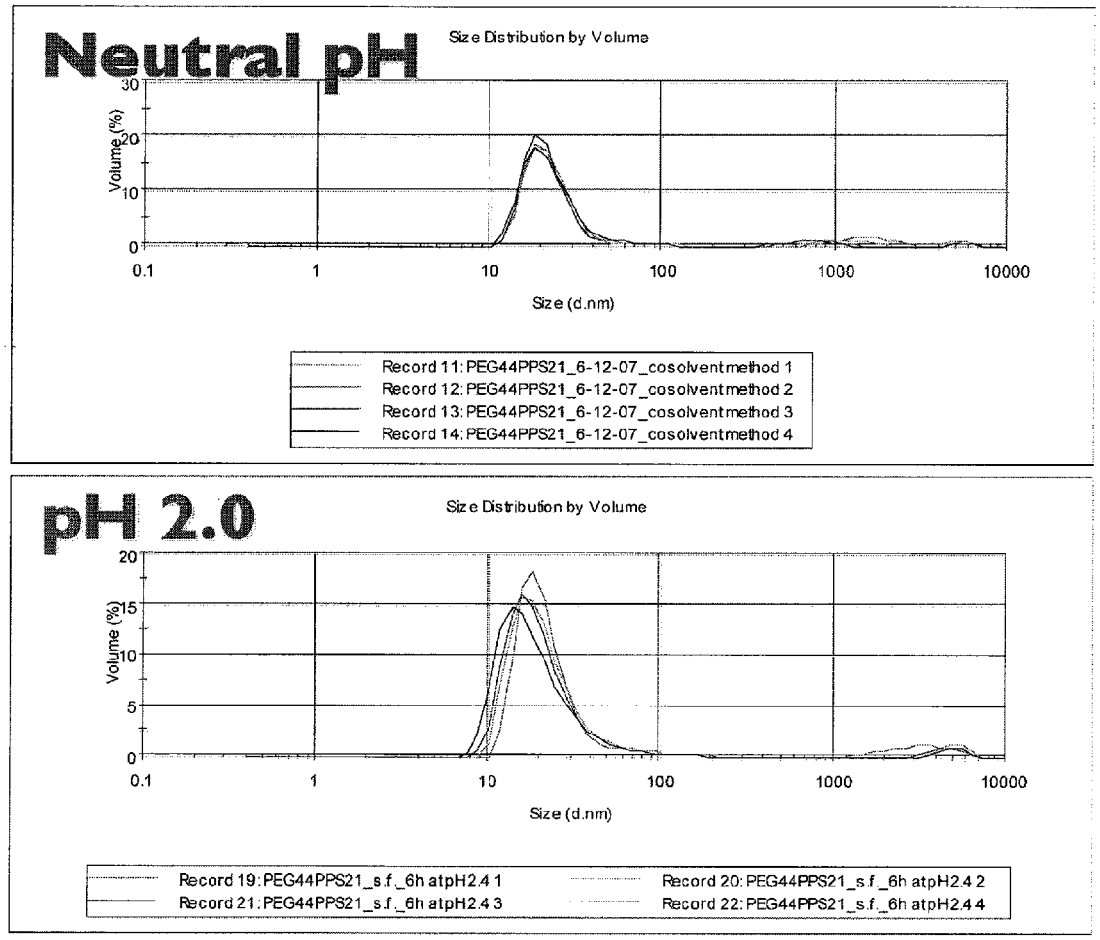
FIG. 17B. Stability of $PEG_{44}$-$PPS_{20}$ after exposure to gastric pH, as measured by dynamic light scattering.

Formulations that can solubilize hydrophobic pharmaceutical agents and can be administered in dry form are useful in a number of pharmaceutical applications. We have demonstrated that PEG-PPS micelles can be dried into a tablet and subsequently resuspended rapidly, to the same size distribution, without loss of encapsulated pharmaceutical agent. For example, $PEG_{44}$-$PPS_{20}$ micelles were formed with size mean of 21 nm (FIG. 16A), loaded with cyclosporine A. The suspension was dried, and then the dried sample was placed in water to allow brief rehydration. The measured size distribution showed a mean of 20.3 nm (FIG. 16B). Throughout the process, high encapsulation efficiency was maintained (Table 7). The particles, being primarily sensitive to oxidation, are stable at gastric pH (FIG. 17).

TABLE 7

High loading of cyclosporine A (CsA) was obtained in $PEG_{44}$-$PPS_{20}$ micelles, and this loading was maintained after the micelle suspension was dried at 80° C. and rehydrated in water.

| Polymer | CsA added (mg) | CsA loading (mg/mg) | Encapsulation efficiency (%) | Mean aggregate sixe (nm) |
|---|---|---|---|---|
| $PEG_{44}$-$PPS_{20}$ | 4 | 0.130 | 64 | 21 |
| $PEG_{44}$-$PPS_{20}$ after rehydration | 4 | 0.123 | 62 | 20 |

Example 6

Figure 18:
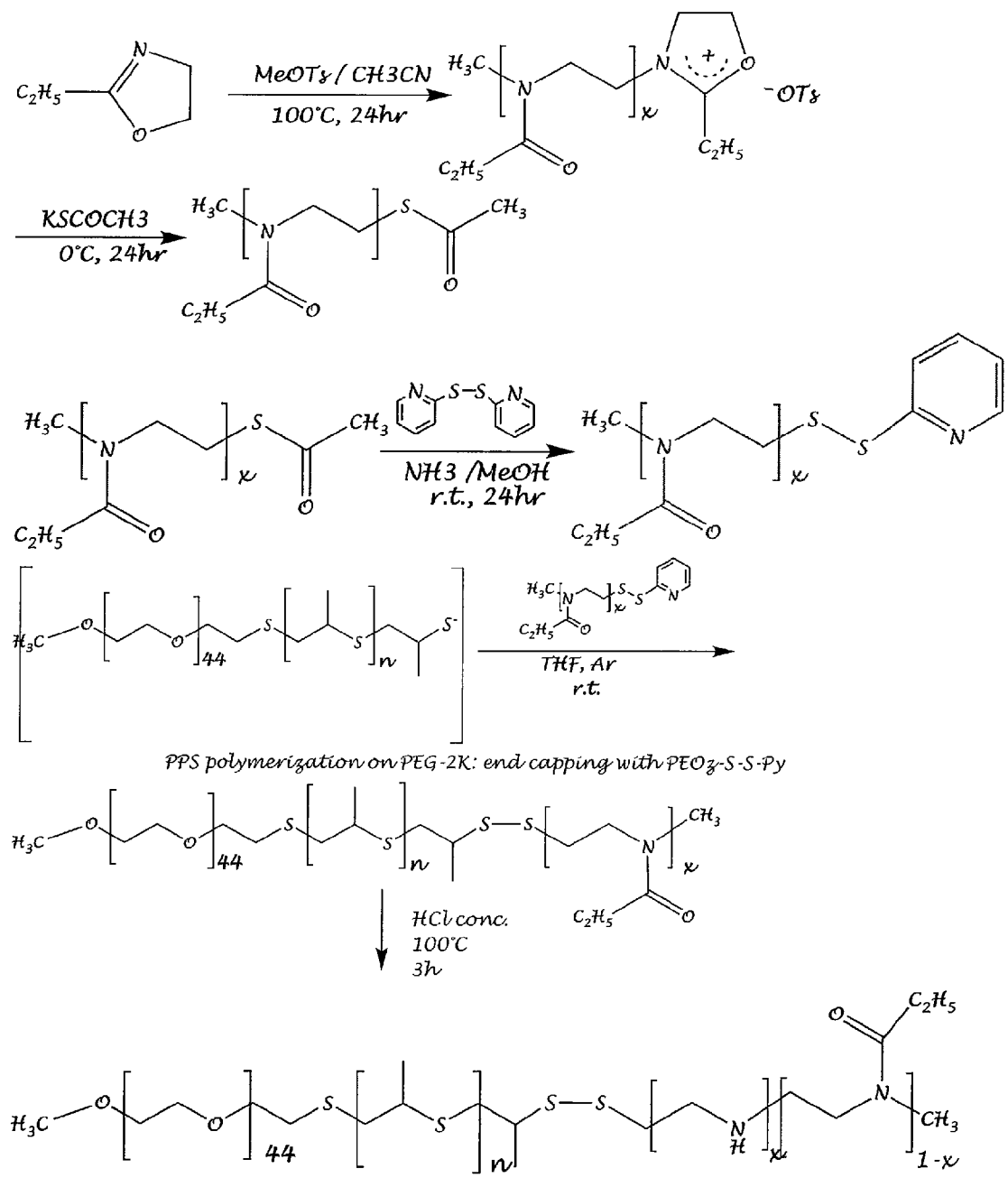
FIG. 18. A synthetic route to PEG-PPS-PEI. A disulfide link between the PPS block and the PEI block allows destabilization of the polymer after endocytosis.
Figure 21:
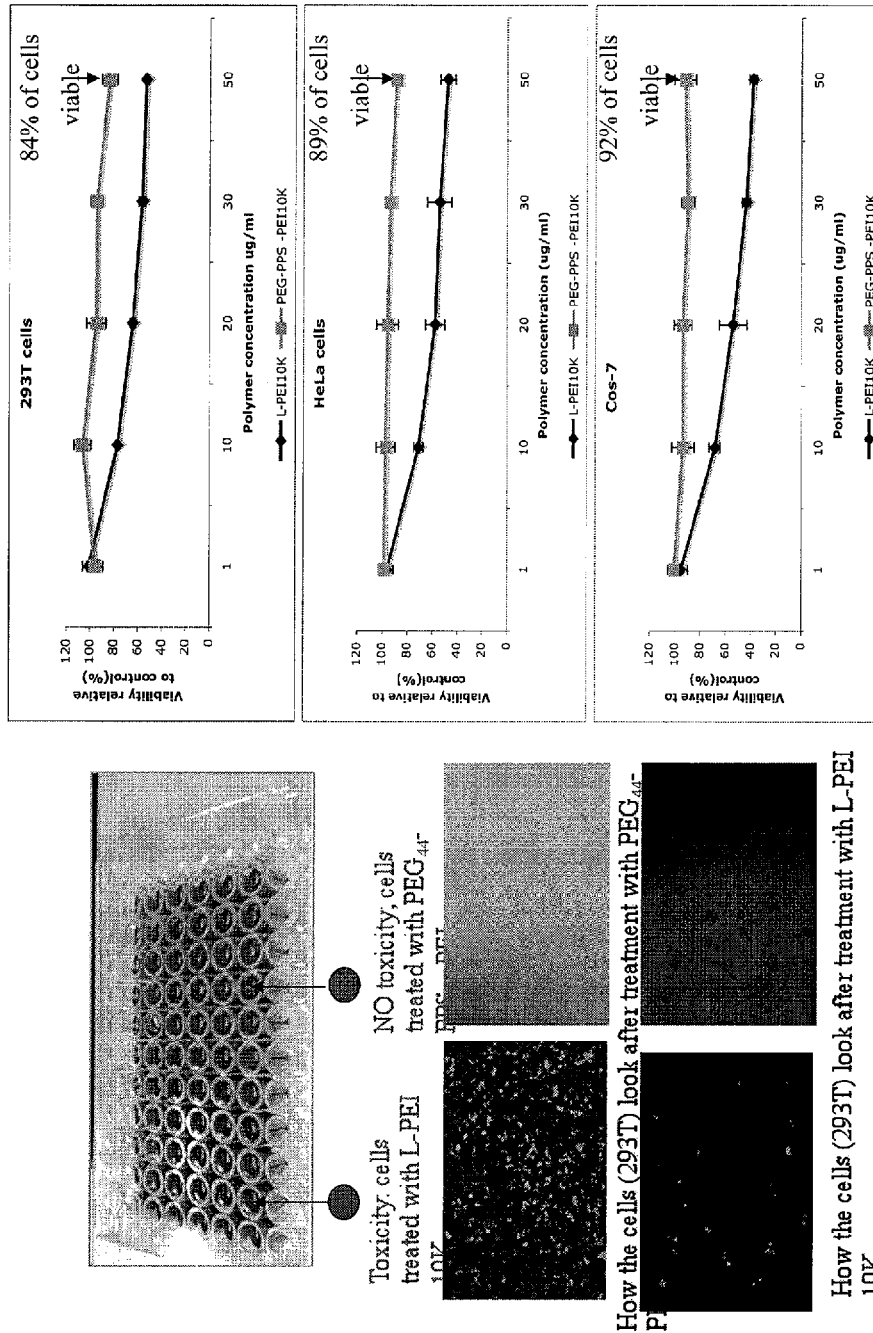
FIG. 21. Cytotoxicity with PEG-PPS-PEI was much lower than that with linear PEI of the same molecular weight at the same PEI concentration.

PEG-PPS-PEI Copolymers can Efficiently Deliver Gene-Based Pharmaceutical Agents Previous work described, among other embodiments, PEG-PPS-polycation triblock copolymers, including the case where the polycation blocks were based on peptides. We have developed easier synthetic routes to analogous polymers, including PEG-PPS-PEI block copolymers (FIG. 18). These copolymers achieve high transfection efficiency, both with plasmid DNA and also with siRNA. The polymers also demonstrated much lower cytotoxicity than did linear PEI of the same PEI molecular weight at the same PEI concentration. These results are shown in FIGS. 19-21.

Example 7

Figure 22:
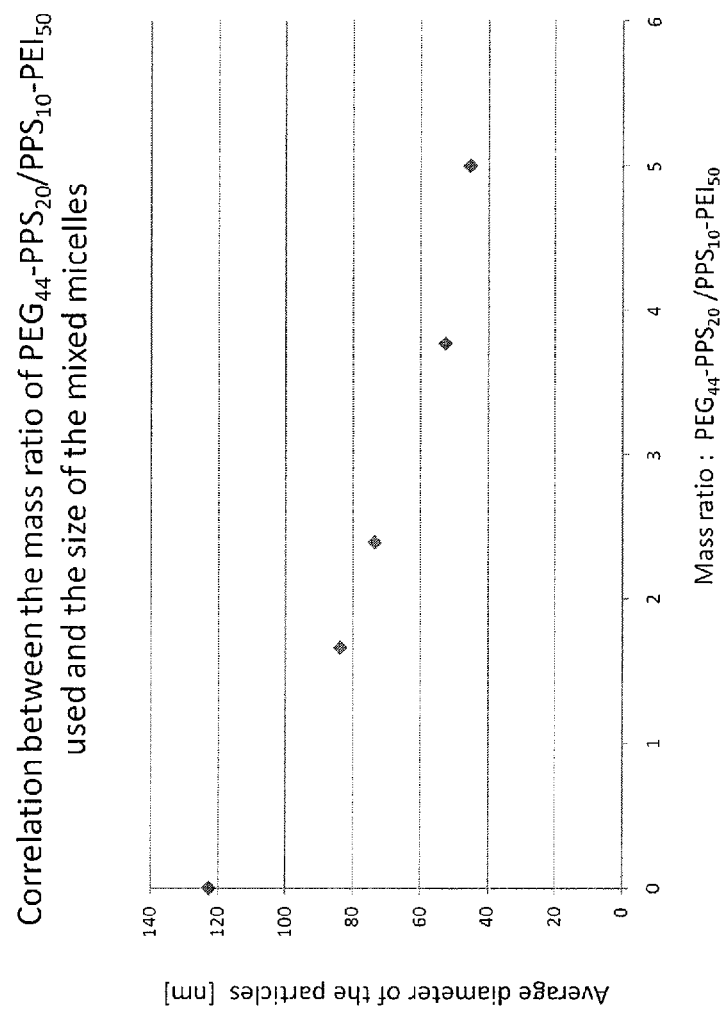
FIG. 22. The size of the resulting gene pharmaceutical agent complexes could be controlled by a number of means, including the ratio of the polymers used to construct mixed micelles.
Figure 23:
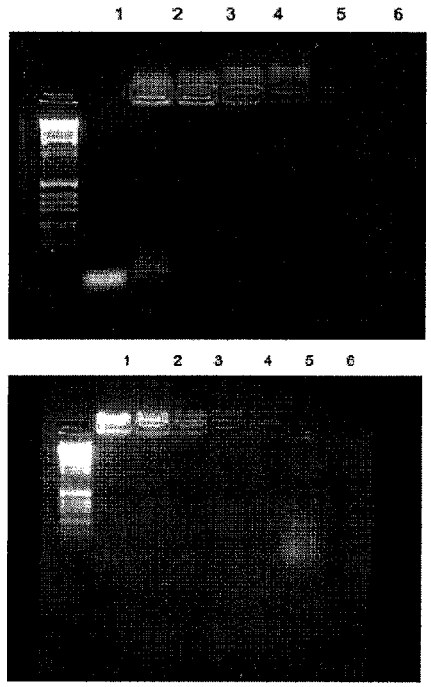
FIG. 23. PEG-PPS-based polymers were able to condense oligonucleotide pharmaceutical agents here with an siRNA sequence, for example to prevent gel migration. This demonstrates the versatility of these polymers with oligonucleotides sequences as well as plasmid DNA.
Figure 24:
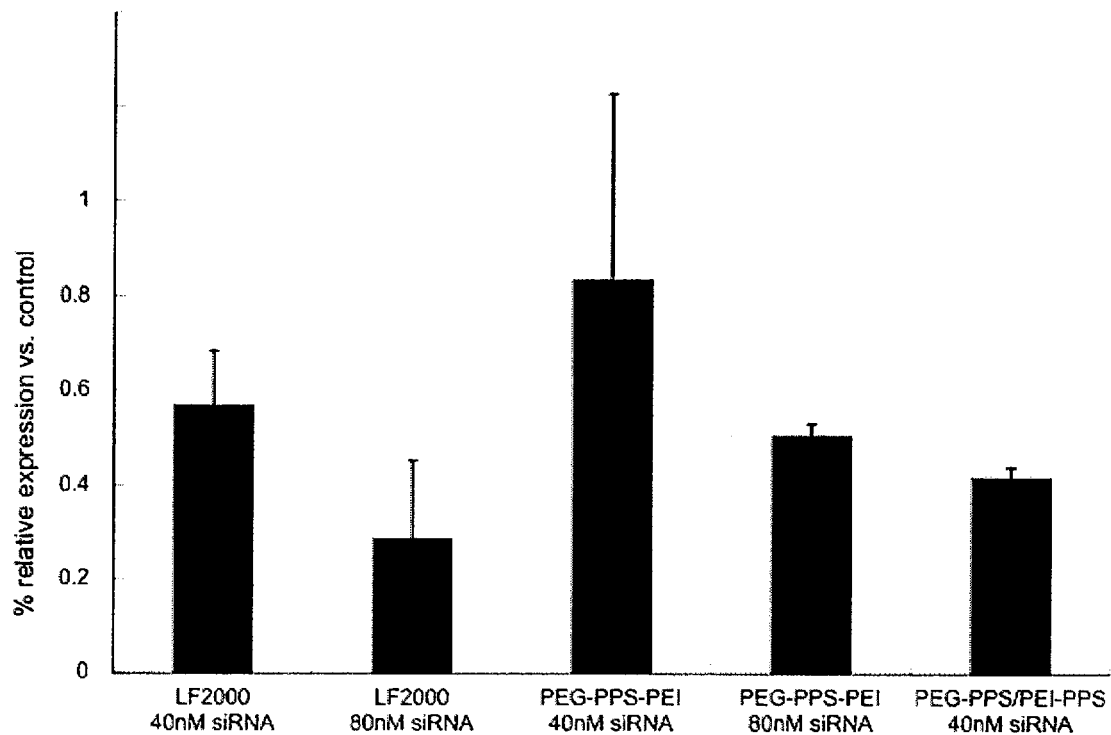
FIG. 24. PEG-PPS-based polymers were able to induce high transfection efficiency with oligonucleotides pharmaceutical agents here with siRNA knocking down expression of lamin A/C in HeLa cells.

Blends of PEG-PPS and PPS-PEI can Form Very Small Complexes with Gene-Based Pharmaceutical Agents It is sometimes particularly desirable to obtain nanoparticles with gene-based pharmaceutical agents that are very small. This was possible by using mixed micelles of PEG-PPS and PPS-PEI to obtain very small complexes. Results with this approach are shown in Table 8 and FIGS. 22-24. It is also possible to incorporate hydrophobic agents within the PPS domains of these complexes to induce an additional effect, such as present a bioactive agent or deliver an agent that enhances transfection efficiency.

As mentioned above, the ultrasmall size of the polymer micelles and other particles may be important; the sizes formed by this method may be particularly useful in some applications. For example, in targeting tumors from the bloodstream via the enhanced permeation and retention effect, in penetration of the arterial wall under physiological pressure or mild overpressure, in penetration of the fenestrated endothelium in the tumor microcirculation, in penetration of mucosal surfaces and targeting cells beneath, such as dendritic cells, and in targeting the lymphatics in the gut, smaller particles are more effective than larger particles.

TABLE 8

PEG-PPS/PPS-PEI mixed micelles condense gene-based pharmaceutical agents into very small nanoparticles.

| Polymer | Size of the particles alone | Size of the particles complexed with siRNA | Size of the particles complexed with DNA |
|---|---|---|---|
| $PEG_{44}$-$PPS_{27}$-$PEI_{96}$ | ~160 nm | ~150 nm | ~180 nm |
| $PEG_{44}$-$PPS_{20}$-$PEI_{70}$ | ~170 nm | ~160 nm | — |
| $PEG_{44}$-$PPS_{20}$/$PPS_{10}$-$PEI_{50}$ | ~60 nm | ~40 nm | ~45 nm |

Example 8

Figure 25:
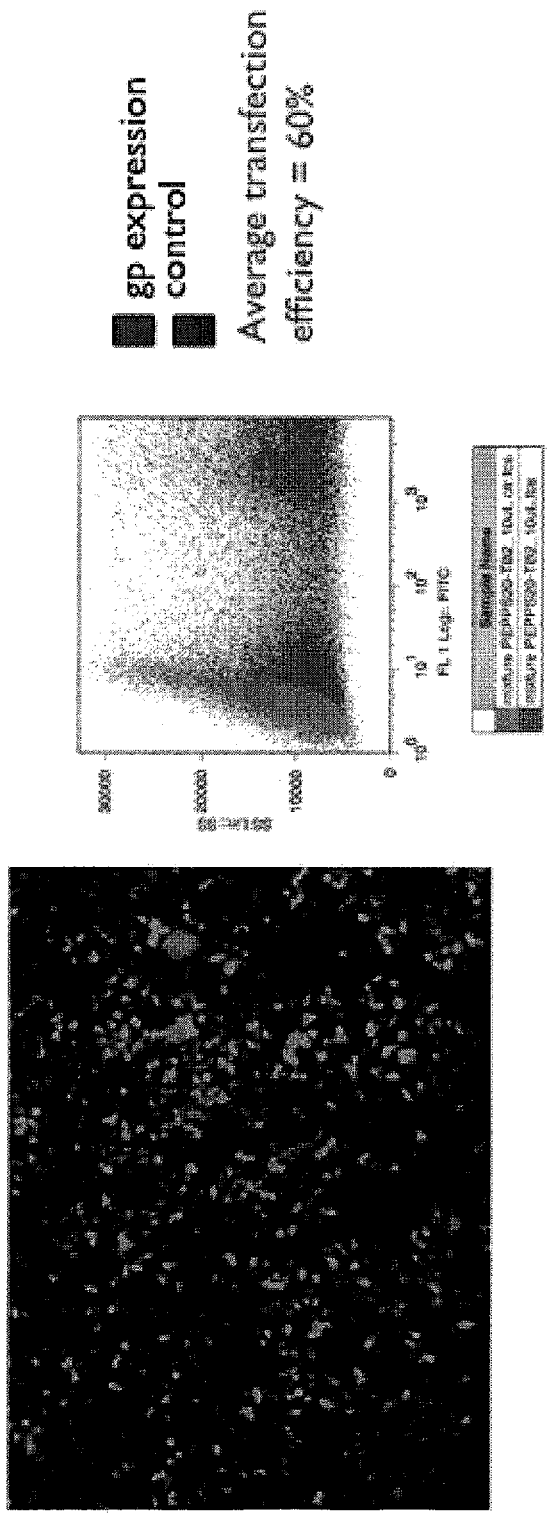
FIG. 25. Gene complexes formed with a 10:1 ratio of PEG-PPS-PEI:PEG-PPS efficiently transfect cells. PEG-PPS was used to reduce the size of PEG-PPS-PEI micelles resulting in smaller complexes with gene-based pharmaceutical agents. Here, cells were incubated with 30 nm complexes containing the green fluorescent protein (GFP) gene sequence.

Blends of PEG-PPS and PEG-PPS-PEI can Form Very Small Complexes with Gene-Based Pharmaceutical Agents In many situations of gene and gene-based pharmaceutical agent delivery (plasmid DNA, siRNA, antisense oligonucleotides, aptamers, or microRNA, for example), the size of the particle is critical for effective delivery. Small particles penetrate tissues better than larger particles and may also lead to higher cytoplasmic delivery and transfection efficiency. For example, complex delivery to tumor beds is more effective with very small complexes. The gene complexes formed from PEG-PPS-PEI can be substantially reduced in size by incorporation of PEG-PPS in the micelle into which the gene is incorporated. As such, the gene-non-binding PEG-PPS drives the formation of smaller size micelles from PEG-PPS-PEI. FIG. 25 demonstrates that ca. 30 nm plasmid DNA complexes can be formed from a 9:1 ratio of PEG-PPS and PEG-PPS-PEI.

Example 9

Surface Modified Nanoparticles

Given that PEG-PPS nanoparticles can survive harsh conditions such as gastric pH, we contemplated their transport in the gut lymphatics, determining their potential to be processed by mechanisms related to fat uptake in the gut. This was measured using a coculture model of caco-2 cells (enterocytes) and lymphatic endothelial cells (LECs), allowing full characterization of uptake, packaging, and transit (collectively referred to as transport). It was determined that the surface characteristics of PPS-based nanoparticles can be engineered to provide for effective transport: for example, particles on which about 10% of the terminal chain groups were substituted with a carboxyl functionality were transported at a level 5-fold higher than that of equivalent particles lacking a surface charge. Other surface charging moieties, such as sulfates and sulfones, are similarly effective after optimization.

The uptake of PEG-PPS nanoparticles is biospecific, as the control macromolecule dextran was not well transported, and the transport was blocked at cold temperatures.

Other surface characteristics also lead to enhanced transport. Particles formed with a terminal hydroxyl group were about 10-fold better transported than analogous particles with terminal methoxy groups. Thus, PPS nanoparticles with 90%-$OCH_3$ and 10% COOH are actively transported across LECs (5× better than others). Moreover, PPS nanoparticles with 90%-OH and 10% COOH are actively transported across Caco-2 cells (10× better than others).

Other Embodiments

The description of the specific embodiments of the invention is presented for the purposes of illustration. It is not intended to be exhaustive nor to limit the scope of the invention to the specific forms described herein. Although the invention has been described with reference to several embodiments, it will be understood by one of ordinary skill in the art that various modifications can be made without departing from the spirit and the scope of the invention, as set forth in the claims. All patents, patent applications, and publications referenced herein are hereby incorporated by reference.

Other embodiments are within the claims.

What is claimed is:

1. A micelle comprising both poly(ethylene glycol)-poly(propylene sulfide) (PEG-PPS) and poly(ethylene glycol)-poly(propylene sulfide)-poly(ethyleneimine) (PEG-PPS-PEI) block copolymers.

2. The micelle of claim 1, wherein said micelle is between 20 and 50 nm in diameter.

3. The micelle of claim 1, wherein the PEG-PPS-PEI copolymer comprises a bond between the PPS and PEI block that is labile in an endosome.

4. The micelle of claim 3, wherein said labile bond is selected from the group consisting of vinyl ether, orthoester, acyl hydrazone, a disulfide bond, or a —N—$PO_3$— group.

5. The micelle of claim 1, wherein the PEG-PPS-PEI block further comprising a nucleic acid complexed to PEI.

6. The micelle of claim 5, wherein said nucleic acid is selected from the group consisting of a single stranded oligonucleotide, an antisense oligonucleotide a small interfering RNA (siRNA), an aptamer, or plasmid DNA.

7. A pharmaceutical composition comprising the block copolymer of claim 1 and further comprising a pharmaceutically acceptable diluent.

8. A dry formulation comprising the micelles of claim 1, wherein said formulation comprises less than 5% water by weight.

9. The formulation of claim 8, wherein said formulation comprises less than 2% water by weight.

10. A method of transfecting a cell with a nucleic acid comprising contacting said cell with the micelle of claim 5.

11. A method of transfecting a cell with a nucleic acid comprising contacting said cell with the micelle of claim 6.

* * * * *

UNITED STATES PATENT AND TRADEMARK OFFICE
CERTIFICATE OF CORRECTION

PATENT NO. : 9,271,929 B2
APPLICATION NO. : 13/130892
DATED : March 1, 2016
INVENTOR(S) : Dixon et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 188 days.

Signed and Sealed this
Twenty-first Day of June, 2016

Michelle K. Lee
*Director of the United States Patent and Trademark Office*